US012728267B2

(12) United States Patent
Vansickle et al.

(10) Patent No.: US 12,728,267 B2
(45) Date of Patent: Sep. 8, 2026

(54) AUTOMATING BOLUS STIMULATION THERAPY FROM LEARNED USAGE

(71) Applicant: Boston Scientific Neuromodulation Corporation, Valencia, CA (US)

(72) Inventors: Dennis Allen Vansickle, Lancaster, CA (US); Que T. Doan, West Hills, CA (US); Esteban Alonso Ortiz Cubero, San Jose (CR); Vuong Tuan Nguyen, Glendale, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 478 days.

(21) Appl. No.: 18/218,538

(22) Filed: Jul. 5, 2023

(65) Prior Publication Data

US 2024/0017067 A1 Jan. 18, 2024

Related U.S. Application Data

(60) Provisional application No. 63/388,716, filed on Jul. 13, 2022.

(51) Int. Cl.
*A61N 1/36* (2006.01)
*A61N 1/372* (2006.01)

(52) U.S. Cl.
CPC ..... *A61N 1/36062* (2017.08); *A61N 1/36167* (2013.01); *A61N 1/37247* (2013.01)

(58) Field of Classification Search
CPC ............ A61N 1/36062; A61N 1/36167; A61N 1/36053; A61N 1/36071; A61N 1/36146; A61N 1/36164; A61N 1/37247
See application file for complete search history.

(56) References Cited

U.S. PATENT DOCUMENTS 8,155,749 B2 4/2012 Lee et al.
8,606,362 B2 12/2013 He et al.
(Continued)

FOREIGN PATENT DOCUMENTS

WO WO-2024015240 A1 1/2024

OTHER PUBLICATIONS

"European Application Serial No. 23745708.0, Response to Communication pursuant to Rules 161 and 162 EPC filed Aug. 18, 2025", 13 pgs.

(Continued)

*Primary Examiner* — Joseph M Dietrich
(74) *Attorney, Agent, or Firm* — Schwegman Lundberg & Woessner, P.A.

(57) ABSTRACT

Systems and methods for controlling neurostimulation based on patient past usage pattern of stimulation therapy are disclose. An exemplary electrostimulation system comprises an electrostimulator to provide a bolus stimulation therapy (BST) to a neural target. The BST comprises stimulation boluses each comprising stimulation pulses during a first duration, any two consecutive boluses being separated by a stimulation-free second duration. A controller circuit can receive information about BST setting and past BST usage in the patient, analyze a BST usage pattern of the patient based on the received information, and determine or adjust a future BST schedule based at least on the BST usage pattern. The electrostimulator can deliver BST to the neural target in accordance with the BST setting and the determined or adjusted future BST schedule.

20 Claims, 13 Drawing Sheets

(56) References Cited

U.S. PATENT DOCUMENTS

| | | | |
|---|---|---|---|
| 8,620,436 | B2 | 12/2013 | Parramon et al. |
| 10,055,550 | B2 | 8/2018 | Goetz |
| 10,786,672 | B2 | 9/2020 | Walker et al. |
| 2015/0231402 | A1 | 8/2015 | Aghassian |
| 2015/0360038 | A1 | 12/2015 | Zottola et al. |
| 2016/0144183 | A1 | 5/2016 | Marnfeldt |
| 2016/0342762 | A1* | 11/2016 | Goetz .................... G16H 40/63 |
| 2017/0080234 | A1* | 3/2017 | Gillespie ............ A61N 1/36025 |
| 2018/0071513 | A1 | 3/2018 | Weiss et al. |
| 2018/0071520 | A1 | 3/2018 | Weerakoon et al. |
| 2019/0126039 | A1 | 5/2019 | Yoo et al. |
| 2020/0353255 | A1 | 11/2020 | Agnesi et al. |
| 2020/0353269 | A1* | 11/2020 | Agnesi ............... A61N 1/37241 |

OTHER PUBLICATIONS

"International Application Serial No. PCT/US2023/026953, International Preliminary Report on Patentability mailed Jan. 23, 2025", 9 pgs.
"International Application Serial No. PCT/US2023/026953, International Search Report mailed Oct. 18, 2023", 4 pgs.
"International Application Serial No. PCT/US2023/026953, Written Opinion mailed Oct. 18, 2023", 7 pgs.

* cited by examiner 17
16
18
15
20
22
10
12
(Ec)
24
26a
23
14
26b
28

34
16
10
15'
15
32
36
42a
42b
44
40

F
+A
30b
PW
30a
IP
-A
E5:
E4:

900C

CONFIGURE BOLUS STIMULATION THERAPY

THERAPY DURATION 02 H 30 M 30 S

BST ON TIME: 02 H 30 M 30 S

BST OFF TIME: 02 H 30 M 30 S

APPLY CANCEL

AUTOMATING BOLUS STIMULATION THERAPY FROM LEARNED USAGE

CLAIM OF PRIORITY

This application claims the benefit of U.S. Provisional Application No. 63/388,716, filed on Jul. 13, 2022, which is hereby incorporated by reference in its entirety.

TECHNICAL FIELD

This document relates generally to medical devices, and more particularly, to an automated bolus stimulation therapy adapted to patient usage pattern of the therapy.

BACKGROUND

Neuromodulation (or "neural neuromodulation", also referred to as "neurostimulation" or "neural stimulation") has been proposed as a therapy for a number of conditions. Often, neuromodulation and neural stimulation may be used interchangeably to describe excitatory stimulation that causes action potentials as well as inhibitory and other effects. Examples of neuromodulation include Spinal Cord Stimulation (SCS), Deep Brain Stimulation (DBS), Peripheral Nerve Stimulation (PNS), and Functional Electrical Stimulation (FES). SCS systems have been used as a therapeutic modality for the treatment of chronic pain syndromes. PNS has been used to treat chronic pain syndrome and incontinence, with a number of other applications under investigation. FES systems have been applied to restore some functionality to paralyzed extremities in spinal cord injury patients. DBS can be used to treat a variety of diseases or disorders.

Stimulation systems, such as implantable electrostimulators, have been developed to provide therapy for a variety of treatments. An implantable electrostimulator can include a pulse generator and one or more leads each including a plurality of stimulation electrodes. The stimulation electrodes are in contact with or near target tissue to be stimulated, such as nerves, muscles, or other tissue. The control module generates a control signal to the pulse generator, which generates electrostimulation pulses that are delivered by the electrodes to the target tissue in accordance with an electrode configuration and a set of stimulation parameters.

Paresthesia-based spinal cord stimulation (SCS) has been used to treat chronic pain. Paresthesia is a sensation such as tingling, prickling, heat, cold, etc. that can accompany SCS therapy. Alternatively, SCS may be delivered with reduced stimulation intensity below a paresthesia threshold to avoid inducing paresthesia, yet still achieve analgesia effect and clinically effective pain relief. Such paresthesia-free SCS, also known as sub-perception SCS, generally uses stimulation pulses at higher frequencies to achieve the paresthesia-free effect, which may consume more power than paresthesia-based SCS.

SUMMARY

Conventional sub-perception SCS has some drawbacks including prolonged wash-in time. For example, in contrast to paresthesia-based SCS in which analgesia is usually observed within minutes, conventional sub-perception SCS typically takes several hours to days until maximum or therapeutically effective analgesia effect can be achieved. Patients treated with conventional sub-perception therapies do not typically receive pain relief during their programming visit, and the effectiveness of the treatment cannot be immediately assured. Additionally, conventional sub-perception electrostimulation (e.g., SCS) generally uses higher-frequency pulses, therefore consumes more power and tends to drain the battery of an implantable pulse generator more quickly and shortens the battery life. Furthermore, therapy optimization can be a complex and onerous process for the conventional sub-perception SCS.

An improved sub-perception SCS, referred to as Fast-Acting Sub-Perception Therapy (FAST), has emerged as a highly effective and energy-efficient sub-perception SCS program. The FAST methodology utilizes a stimulation frequency at a level below 100 Hz (or in some instances lower than 10 Hz) and a biphasic-symmetric waveform comprising an active charge phase followed by an active charge recovery phase (also referred to as a recharge phase). FAST may be used to activate various neural targets including, for example, dorsal columns, peripheral nerves, DRG, or dorsal roots, among other neural structures. Compared to conventional sub-perception SCS therapies that uses passive-recharge pulses, FAST can achieve fast-acting analgesia, significantly reduce the wash-in time, and achieve significant and long-lasting pain relief (about six months after being activated in an example).

Some SCS systems include an external controller that allows the patient to select one of pre-generated stimulation programs or to control various stimulation parameters, such as stimulation intensity, duration, etc. The patient can self-administer therapy at will without returning to the physician for review of effectiveness or follow-up. Allowing the patient the unfettered ability to self-medicate (e.g., programming the stimulation) may potentially lead to stimulation overuse and develop patient tolerance to stimulation. Overstimulation can reduce the effectiveness of therapy even in the absence of other side effects. For example, a patient may increase the frequency and/or intensity of their stimulation in an effort to compensate for a decrease in the effectiveness of their therapy. But such increases in stimulation may accelerate the rate at which the patient develops a tolerance to the stimulation, thereby negatively impacting the patient's therapy. The present inventors have recognized an unmet need for improved neuromodulation systems and methods that can help avoid or reduce the chances of stimulation overuse, and provide automated and individualized therapy titration (or recommendations thereof) based on patient medical needs and past experiences or usage pattern of certain stimulation programs. Such systems and methods would improve the therapy efficacy and patient management efficiency, and reduce physicians workload for manage patients.

Various examples discussed in this document may improve the efficacy of sub-perception SCS stimulation and automaticity of therapy programming based on patient past experience such as a usage pattern of sub-perception SCS stimulation. According to one embodiment, an electrostimulation system comprises an electrostimulator and a controller circuit. The electrostimulator can provide stimulation energy to a neural target of the patient. The stimulation energy may be provided in discreet chunks of stimulation pulses, referred to as "boluses" of stimulation. After a bolus is issued, further stimulation is not provided until another bolus is issued. A bolus stimulation therapy (BST) thus comprises boluses of stimulation each comprising stimulation pulses delivered during a first duration to the neural target, while any two consecutive boluses are separated by a stimulation-free second duration. The controller circuit can receive information about BST setting and past BST usage in the patient, such as from a user (e.g., the patient) or from a storage device that stores records of past BST usage, analyze a BST usage pattern of the patient based on the received information, and determine or adjust a future BST schedule based at least on the BST usage pattern. The electrostimulator can deliver BST to the neural target in accordance with the BST setting and the determined or adjusted future BST schedule.

Example 1 is a system for providing electrostimulation to a patient, comprising: an electrostimulator configured to provide a bolus stimulation therapy (BST) to a neural target of the patient, the BST comprising boluses of stimulation each comprising stimulation pulses delivered during a first duration to the neural target, any two consecutive boluses being separated by a stimulation-free second duration; and a controller circuit configured to: receive information about a BST setting and past BST usage in the patient; analyze a BST usage pattern based on the received information about the past BST usage; determine or adjust a future BST schedule based at least on the BST usage pattern; and generate a control signal to the electrostimulator to deliver BST to the neural target in accordance with the BST setting and the determined or adjusted future BST schedule.

In Example 2, the subject matter of Example 1 optionally includes, wherein the received information about the past BST usage includes timing or duration for activating the BST during a past time period, wherein the controller circuit is configured to analyze the BST usage pattern based on a comparison of the timing or duration for activating the BST over the past time period.

In Example 3, the subject matter of Example 2 optionally includes, wherein to analyze the BST usage pattern includes to identify a majority of substantially consistent timing or duration for activating the BST during the past time period, wherein the controller circuit is configured to determine or adjust the future BST schedule including future timing or duration for activating the BST based on the identified majority of substantially consistent timing or duration.

In Example 4, the subject matter of any one or more of Examples 2-3 optionally includes, wherein the controller circuit is configured to analyze the BST usage pattern at a user-specified frequency.

In Example 5, the subject matter of any one or more of Examples 1-4 optionally includes, wherein the received information about the past BST usage includes information about usage of a specific stimulation program during a past time period, wherein the controller circuit is configured to analyze the BST usage pattern to determine a frequent use of the specific stimulation program.

In Example 6, the subject matter of Example 5 optionally includes, wherein the specific stimulation program includes a sub-perception stimulation program comprising biphasic pulses each including an active charge phase and a subsequent reconfigurable active or passive recharge phase.

In Example 7, the subject matter of Example 6 optionally includes, wherein the sub-perception stimulation program comprises, within a bolus of a plurality of biphasic pulses, a first portion of the biphasic pulses each having an active recharge phase and a second portion of the biphasic pulses each having a passive recharge phase, wherein the controller circuit is configured to determine or adjust the future BST schedule by decreasing a first number of the biphasic pulses with active recharge phases or increasing a second number of biphasic pulses with passive recharge phases over time.

In Example 8, the subject matter of Example 7 optionally includes, wherein the controller circuit is configured to decrease the first number or to increase the second number at respective adjustable rates.

In Example 9, the subject matter of any one or more of Examples 1-8 optionally includes, wherein the controller circuit is configured to determine or adjust the future BST schedule further based on information about patient response to the BST delivered to the neural target.

In Example 10, the subject matter of Example 9 optionally includes an ambulatory sensor configured to sense signals indicative of the patient response to the BST delivered to the neural target, wherein the controller circuit is configured to determine or adjust the future BST schedule further based on the sensed signals.

In Example 11, the subject matter of any one or more of Examples 1-10 optionally includes, wherein the controller circuit is configured to receive the information about the BST setting and the past BST usage from a storage device configured to automatically store information about BST being delivered to the neural target.

In Example 12, the subject matter of any one or more of Examples 1-11 optionally include a user interface device communicatively coupled to the controller circuit, the user interface device configured to, under a control of the controller circuit, display one or more of the BST usage pattern or the determined or adjusted future BST schedule.

In Example 13, the subject matter of Example 12 optionally includes, wherein the user interface device is configured to display a calendar view of one or more of the BST usage pattern or the determined or adjusted future BST schedule.

In Example 14, the subject matter of any one or more of Examples 12-13 optionally includes, wherein the user interface device is configured to: display the determined or adjusted future BST schedule including a recommendation for date, time, duration, stimulation parameter values, or stimulation program; and receive a user input to confirm, reject, or modify the recommendation.

In Example 15, the subject matter of any one or more of Examples 12-14 optionally includes, wherein the user interface device is configured to display a progress of the BST being delivered to the neural target of the patient.

Example 16 is a method for providing a bolus stimulation therapy (BST) to a patient, the method comprising: receiving, from a user input device or a storage device, information about a BST setting and past BST usage in the patient; analyzing a BST usage pattern based on the received information about the past BST usage; determining or adjusting a future BST schedule based at least on the BST usage pattern; and delivering BST to a neural target of the patient in accordance with the BST setting and the determined or adjusted future BST schedule using an electrostimulator, the BST comprising boluses of stimulation each comprising stimulation pulses delivered during a first duration to the neural target, any two consecutive boluses being separated by a stimulation-free second duration.

In Example 17, the subject matter of Example 16 optionally includes, wherein the received information about the past BST usage includes timing or duration for activating the BST during a past time period, and wherein analyzing the BST usage pattern includes identifying a majority of substantially consistent timing or duration for activating the BST during the past time period; wherein determining or adjusting the future BST schedule includes determining or adjusting a future timing or duration for activating the BST based on the identified majority of substantially consistent timing or duration.

In Example 18, the subject matter of any one or more of Examples 16-17 optionally includes, wherein the received information about the past BST usage includes information about usage of a specific stimulation program during a past time period, wherein analyzing the BST usage pattern includes determining a frequent use of the specific stimulation program.

In Example 19, the subject matter of Example 18 optionally includes, wherein the specific stimulation program includes a sub-perception stimulation program comprising biphasic pulses each including an active charge phase and a subsequent reconfigurable active or passive recharge phase.

In Example 20, the subject matter of Example 19 optionally includes, wherein the sub-perception stimulation program comprises, within a bolus of a plurality of biphasic pulses, a first portion of the biphasic pulses each having an active recharge phase and a second portion of the biphasic pulses each having a passive recharge phase, wherein determining or adjusting the future BST schedule includes decreasing a first number of the biphasic pulses with active recharge phases or increasing a second number of biphasic pulses with passive recharge phases over time.

In Example 21, the subject matter of Example 20 optionally includes, wherein decreasing the first number or increasing the second number over time are in accordance with respective adjustable rates.

In Example 22, the subject matter of any one or more of Examples 16-21 optionally include displaying, on a user interface device, a calendar view of one or more of the BST usage pattern or the determined or adjusted future BST schedule.

The description that follows will generally focus on the use of the invention within a Spinal Cord Stimulation (SCS) systems. However, the present invention may find applicability with any implantable neurostimulator device system, including DBS system, Vagus Nerve Stimulation (VNS) system, Sacral Nerve Stimulation (SNS) systems, and the like. For example, apparatus and methods for detecting (and maintaining) exceptionally small evoked neural activities as described herein can be used to detect evoked neural activities in closed-loop DBS therapy, or therapies of other regions of the nervous system. The following examples illustrate various aspects of the examples described herein.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various examples are illustrated by way of example in the figures of the accompanying drawings. Such examples are demonstrative and not intended to be exhaustive or exclusive examples of the present subject matter.

DETAILED DESCRIPTION

This document describes systems and methods for controlling neurostimulation based on patient past experience such as a usage pattern of sub-perception SCS stimulation. According to one embodiment, an electrostimulation system comprises an electrostimulator to provide a bolus stimulation therapy (BST) to a neural target of the patient. The BST comprises boluses of stimulation each comprising stimulation pulses delivered during a first duration to the neural target, where any two consecutive boluses are separated by a stimulation-free second duration. The electrostimulation system comprises a controller circuit to receive information about BST setting and past BST usage in the patient, analyze a BST usage pattern of the patient based on the received information, and determine or adjust a future BST schedule based at least on the BST usage pattern. The controller circuit can generate a control signal to the electrostimulator to deliver BST to the neural target in accordance with the BST setting and the determined or adjusted future BST schedule.

Various examples described herein involve deep brain stimulation (DBS). The following detailed description of the present subject matter refers to the accompanying drawings which show, by way of illustration, specific aspects and examples in which the present subject matter may be practiced. These examples are described in sufficient detail to enable those skilled in the art to practice the present subject matter. Other examples may be utilized and structural, logical, and electrical changes may be made without departing from the scope of the present subject matter. References to "an", "one", or "various" examples in this disclosure are not necessarily to the same example, and such references contemplate more than one example. The following detailed description is, therefore, not to be taken in a limiting sense, and the scope is defined only by the appended claims, along with the full scope of legal equivalents to which such claims are entitled.

Figure 1:
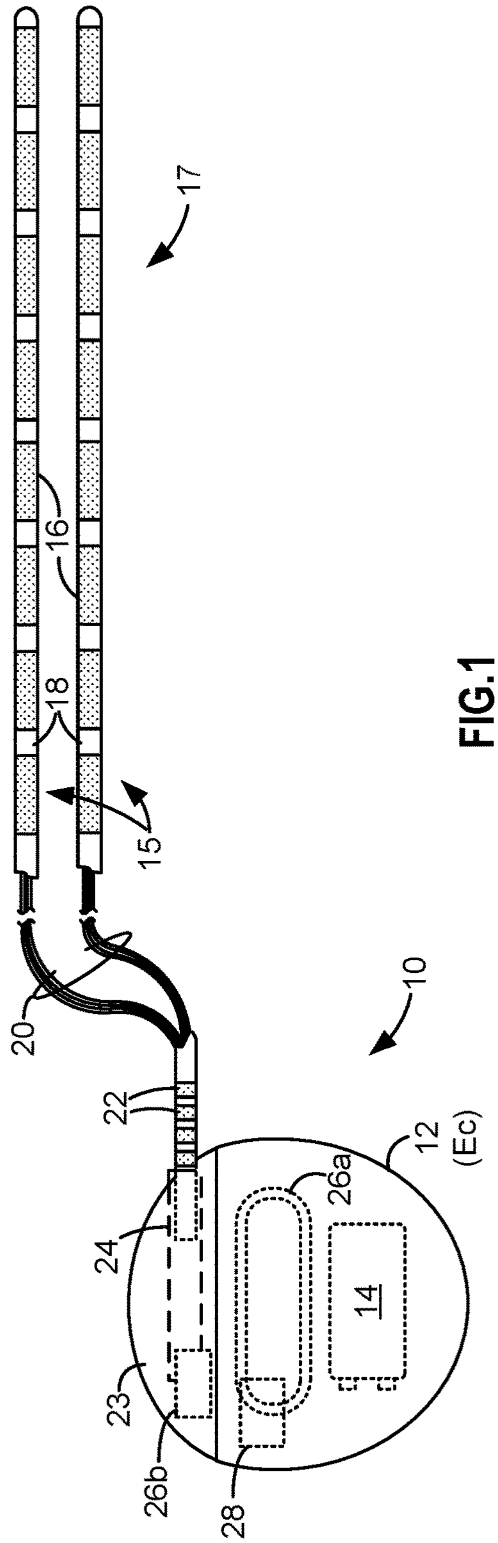
FIG. 1 illustrates, by way of example and not limitation, an Implantable Pulse Generator (IPG) useable for Spinal Cord Stimulation (SCS).

FIG. 1 illustrates, by way of example and not limitation, an Implantable Pulse Generator (IPG) 10 useable for Spinal Cord Stimulation (SCS). The IPG 10 includes a biocompatible device case 12 that holds the circuitry and battery 14 necessary for the IPG to function. The IPG 10 is coupled to electrodes 16 via one or more electrode leads 15 that form an electrode array 17. The electrodes 16 are configured to contact a patient's tissue and are carried on a flexible body 18, which also houses the individual lead wires 20 coupled to each electrode 16. The lead wires 20 are also coupled to proximal contacts 22, which are insertable into lead connectors 24 fixed in a header 23 on the IPG 10, which header can comprise an epoxy for example. Once inserted, the proximal contacts 22 connect to header contacts within the lead connectors 24, which are in turn coupled by feedthrough pins through a case feedthrough to circuitry within the case 12, although these details aren't shown.

By way of example and not limitation, in the illustrated IPG 10, there are sixteen lead electrodes (E1-E16) split between two leads 15, with the header 23 containing a 2×1 array of lead connectors 24. However, the number of leads and electrodes in an IPG is application specific and therefore can vary. The conductive case 12 can also comprise an electrode (Ec). In a SCS application, the electrode leads 15 are typically implanted proximate to the dura in a patient's spinal column on the right and left sides of the spinal cord midline. The proximal contacts 22 are tunneled through the patient's tissue to a distant location such as the buttocks where the IPG case 12 is implanted, at which point they are coupled to the lead connectors 24. In other IPG examples designed for implantation directly at a site requiring stimulation, the IPG can be lead-less, having electrodes 16 instead appearing on the body of the IPG for contacting the patient's tissue. The IPG leads 15 can be integrated with and permanently connected the case 12 in other IPG solutions. The goal of SCS therapy is to provide electrical stimulation from the electrodes 16 to alleviate a patient's symptoms, most notably chronic back pain.

Figure 4:
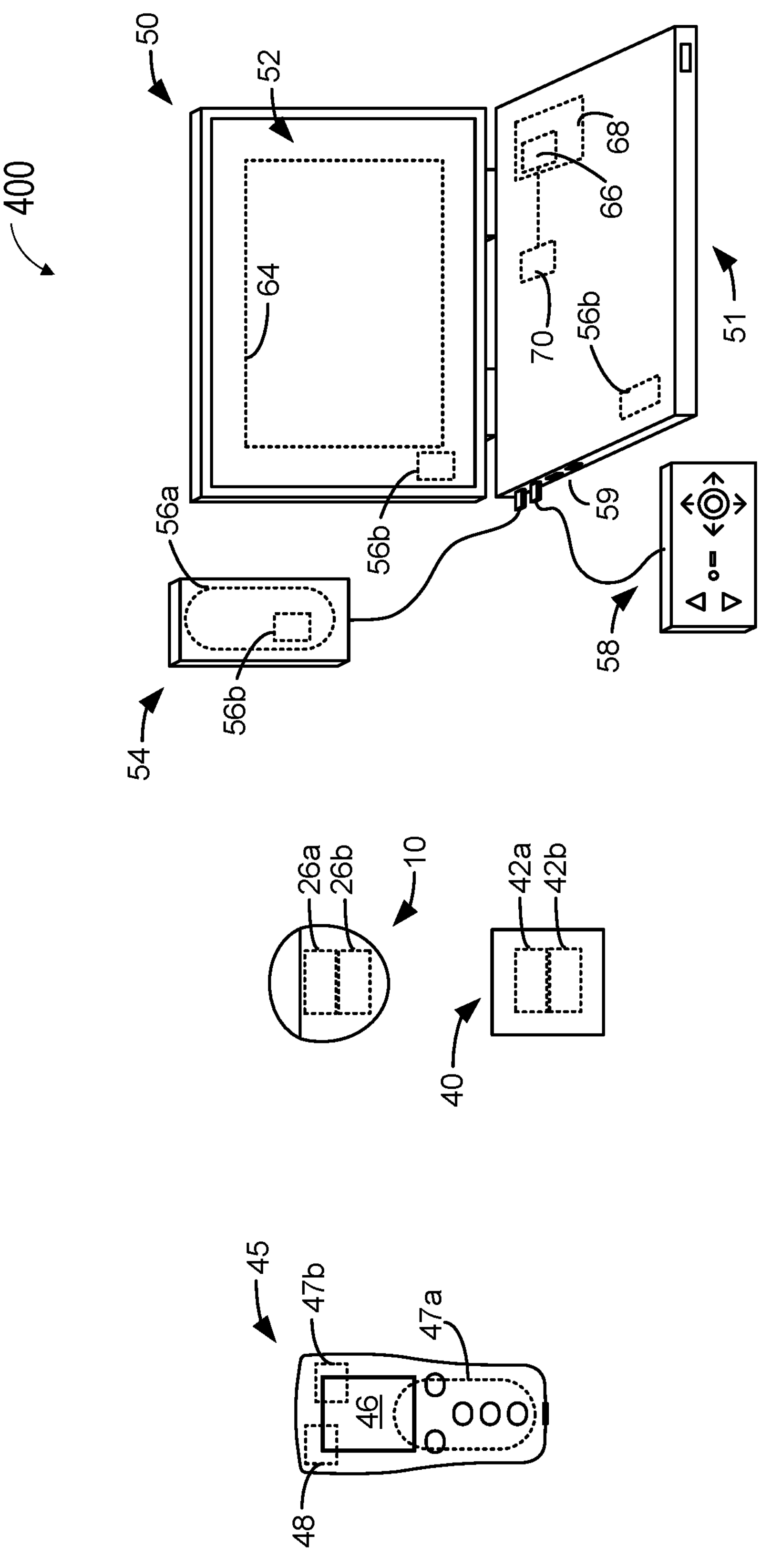
FIG. 4 illustrates, by way of example and not limitation, various external devices capable of communicating with and programming stimulation in an IPG and ETS.

The IPG 10 can include an antenna 26*a* allowing it to communicate bi-directionally with a number of external devices, as shown in FIG. 4. The antenna 26*a* as depicted in FIG. 1 is shown as a conductive coil within the case 12, although the coil antenna 26*a* can also appear in the header 23. When antenna 26*a* is configured as a coil, communication with external devices preferably occurs using near-field magnetic induction. IPG may also include a Radio-Frequency (RF) antenna 26*b*. In FIG. 1, RF antenna 26*b* is shown within the header 23, but it may also be within the case 12. RF antenna 26*b* may comprise a patch, slot, or wire, and may operate as a monopole or dipole. RF antenna 26*b* preferably communicates using far-field electromagnetic waves. RF antenna 26*b* may operate in accordance with any number of known RF communication standards, such as Bluetooth, Zigbee, WiFi, MICS, and the like.

Figure 2:
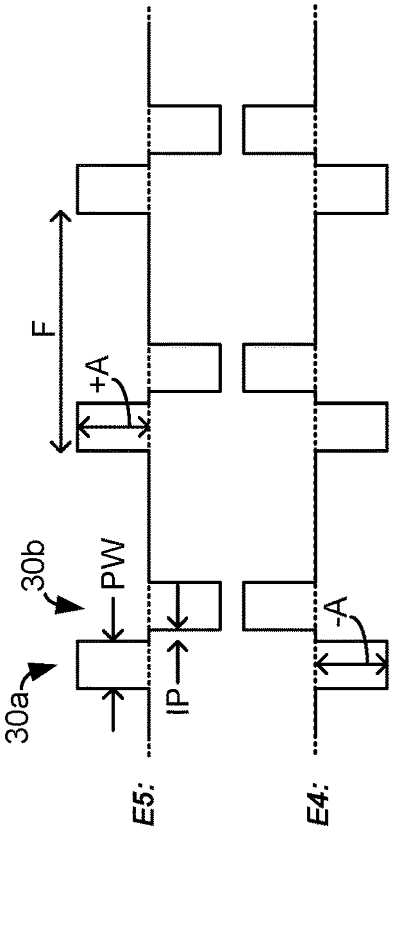
FIG. 2 illustrates, by way of example and not limitation, an example of stimulation pulses producible by an IPG.

Stimulation in the IPG 10 is typically provided by pulses, as shown in FIG. 2. Stimulation parameters typically include the amplitude of the pulses (A; whether current or voltage); the frequency (F) and pulse width (PW) of the pulses; the electrodes 16 (E) activated to provide such stimulation; and the polarity (P) of such active electrodes, i.e., whether active electrodes are to act as anodes (that source current to the tissue) or cathodes (that sink current from the tissue). These stimulation parameters taken together comprise a stimulation program that the IPG 10 can execute to provide therapeutic stimulation to a patient.

FIG. 2 illustrates, by way of example and not limitation, an example of stimulation pulses producible by an IPG, such as the IPG 10. In this example, the electrode E5 has been selected as an anode, and thus provides pulses which source a positive current of amplitude +A to the tissue. Electrode E4 has been selected as a cathode, and thus provides pulses which sink a corresponding negative current of amplitude −A from the tissue. This is an example of bipolar stimulation, in which only two lead-based electrodes are used to provide stimulation to the tissue (one anode, one cathode). However, more than one electrode may act as an anode at a given time, and more than one electrode may act as a cathode at a given time (e.g., tripolar stimulation, quadripolar stimulation, etc.).

The pulses as shown in FIG. 2 are biphasic, comprising a first phase 30*a*, followed quickly thereafter by a second phase 30*b* of opposite polarity. As is known, use of a biphasic pulse is useful in active charge recovery. For example, each electrodes' current path to the tissue may include a serially-connected DC-blocking capacitor, see, e.g., U.S. Patent Application Publication 2016/0144183, which will charge during the first phase 30*a* and discharged (be recovered) during the second phase 30*b*. In the example shown, the first and second phases 30*a* and 30*b* have the same duration and amplitude (although opposite polarities), which ensures the same amount of charge during both phases. In some examples, the second phase 30*b* may be charged balance with the first phase 30*a* if the integral of the amplitude and durations of the two phases are equal in magnitude. The width of each pulse, PW, is defined here as the duration of first pulse phase 30*a*, although pulse width could also refer to the total duration of the first and second pulse phases 30*a* and 30*b* as well. Note that an interphase period during which no stimulation is provided may be provided between the two phases 30*a* and 30*b*.

The IPG 10 includes stimulation circuitry 28 that can be programmed to produce the stimulation pulses at the electrodes as defined by the stimulation program. Stimulation circuitry 28 can for example comprise the circuitry described in U.S. Patent Application Publications 2018/0071513 and 2018/0071520, or in U.S. Pat. Nos. 8,606,362 and 8,620,436. The entirety of such references are incorporated herein by reference.

Figure 3:
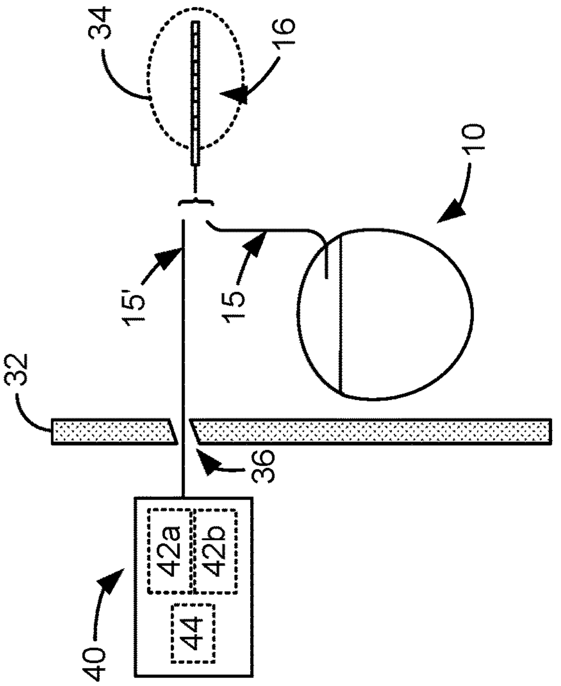
FIG. 3 illustrates, by way of example and not limitation, use of an External Trial Stimulator (ETS) useable to provide stimulation before implantation of an IPG.

FIG. 3 illustrates, by way of example and not limitation, use of an External Trial Stimulator (ETS) 40 useable to provide stimulation, and at least a portion of external trial stimulation environment that may precede implantation of an IPG 10 in a patient. During external trial stimulation, stimulation can be tried on a prospective implant patient without going so far as to implant the IPG 10. Instead, one or more trial leads 15' are implanted in the patient's tissue 32 at a target location 34, such as within the spinal column as explained earlier. The proximal ends of the trial lead(s) 15' exit an incision 36 and are connected to an External Trial Stimulator (ETS) 40. The ETS 40 generally mimics operation of the IPG 10, and thus can provide stimulation pulses to the patient's tissue as explained above. See, e.g., U.S. Pat. No. 9,259,574, disclosing a design for an ETS. The ETS 40 is generally worn externally by the patient for a short while (e.g., two weeks), which allows the patient and his clinician to experiment with different stimulation parameters to try and find a stimulation program that alleviates the patient's symptoms (e.g., pain). If external trial stimulation proves successful, trial lead(s) 15' are explanted, and a full IPG 10 and lead(s) 15 are implanted as described above; if unsuccessful, the trial lead(s) 15' are simply explanted.

Like the IPG 10, the ETS 40 can include one or more antennas to enable bi-directional communications with external devices, explained further with respect to FIG. 4. Such antennas can include a near-field magnetic-induction coil antenna 42*a*, and/or a far-field RF antenna 42*b*, as described earlier. ETS 40 may also include stimulation circuitry 44 able to form the stimulation pulses in accordance with a stimulation program, which circuitry may be similar to or comprise the same stimulation circuitry 28 present in the IPG 10. ETS 40 may also include a battery (not shown) for operational power.

FIG. 4 illustrates at least a portion of a neuromodulation system 400. The neuromodulation system 400 comprises the IPG 10 and the ETS 40 as described above with reference to FIGS. 1-3, and various external devices capable of communicating with and programming stimulation in the IPG 10 and the ETS 40, including a patient, hand-held external remote controller (RC) 45, and a clinician programmer (CP) 50. Both the RC 45 and the CP 50 can be used to send a stimulation program to the IPG 10 or ETS 40—that is, to program their stimulation circuitries 28 and 44 to produce pulses with a desired shape and timing described earlier. Both devices 45 and 50 may also be used to adjust one or more stimulation parameters of a stimulation program that the IPG 10 or ETS 40 is currently executing. Devices 45 and 50 may also receive information from the IPG 10 or ETS 40, such as various status information, etc.

The RC 45 can be as described in U.S. Patent Application Publication 2015/0080982 for example, and may comprise a dedicated controller configured to work with the IPG 10. The RC 45 may also comprise a general purpose mobile electronics device such as a mobile phone which has been programmed with a Medical Device Application (MDA) allowing it to work as a wireless controller for the IPG 10 or ETS 40, as described in U.S. Patent Application Publication 2015/0231402. RC 45 includes a user interface, including means for entering commands (e.g., buttons or icons) and a display 46. The RC 45's user interface enables a patient to adjust stimulation parameters, although it may have limited functionality when compared to the more-powerful CP 50.

In some examples, the RC 45 can have one or more antennas capable of communicating with the IPG 10 and ETS 40. For example, the RC 45 can have a near-field magnetic-induction coil antenna 47*a* capable of wirelessly communicating with the coil antenna 26*a* or 42*a* in the IPG 10 or ETS 40. The RC 45 can also have a far-field RF antenna 47*b* capable of wirelessly communicating with the RF antenna 26*b* or 42*b* in the IPG 10 or ETS 40.

In some examples, the RC 45 can have control circuitry 48 such as a microprocessor, microcomputer, an FPGA, other digital logic structures, an Applicant Specific Integrated Circuit (ASIC), etc., which is capable of executing instructions an electronic device. Control circuitry 48 can for example receive patient adjustments to stimulation parameters, and create a stimulation program to be wirelessly transmitted to the IPG 10 or ETS 40.

The CP 50 can be as described further in U.S. Patent Application Publication 2015/0360038, and is only briefly explained here. The CP 50 can comprise a computing device 51, such as a desktop, laptop, or notebook computer, a tablet, a mobile smart phone, a Personal Data Assistant (PDA)-type mobile computing device, etc. In FIG. 4, computing device 51 is shown as a laptop computer that includes typical computer user interface means such as a screen 52, a mouse, a keyboard, speakers, a stylus, a printer, etc., not all of which are shown for convenience. Also shown in FIG. 4 are accessory devices for the CP 50 that are usually specific to its operation as a stimulation controller, such as a communication "wand" 54, and a joystick 58, which are coupleable to suitable ports on the computing device 51, such as USB ports 59 for example.

The antenna used in the CP 50 to communicate with the IPG 10 or ETS 40 can depend on the type of antennas included in those devices. If the patient's IPG 10 or ETS 40 includes a coil antenna 26*a* or 42*a*, wand 54 can likewise include a coil antenna 56*a* to establish near-filed magnetic-induction communications at small distances. In this instance, the wand 54 may be affixed in close proximity to the patient, such as by placing the wand 54 in a belt or holster wearable by the patient and proximate to the patient's IPG 10 or ETS 40.

In an example where the IPG 10 or ETS 40 includes an RF antenna 26*b* or 42*b*, the wand 54, the computing device 51, or both, can likewise include an RF antenna 56*b* to establish communication with the IPG 10 or ETS 40 at larger distances. (Wand 54 may not be necessary in this circumstance). The CP 50 can also establish communication with other devices and networks, such as the Internet, either wirelessly or via a wired link provided at an Ethernet or network port.

To program stimulation programs or parameters for the IPG 10 or ETS 40, the clinician interfaces with a clinician programmer graphical user interface (GUI) 64 provided on the display 52 of the computing device 51. As one skilled in the art understands, the GUI 64 can be rendered by execution of clinician programmer software 66 on the computing device 51, which software may be stored in the device's non-volatile memory 68. One skilled in the art will additionally recognize that execution of the clinician programmer software 66 in the computing device 51 can be facilitated by control circuitry 70 such as a microprocessor, microcomputer, an FPGA, other digital logic structures, etc., which is capable of executing programs in a computing device. The control circuitry 70 can execute the clinician programmer software 66 to generate a therapy plan and rendering the GUI 64. The therapy plan (also referred to as a stimulation program) may include stimulation parameters chosen through the GUI 64 (e.g., electrode configurations and stimulation dosing parameters). The control circuitry 70 can enable communications via antennas 56*a* or 56*b* to communicate the therapy plan (e.g., stimulation parameters) to the patient's IPG 10. The IPG 10 may deliver electrostimulation in accordance with the therapy plan.

In an example, the therapy plan includes a sub-perception SCS plan comprising stimulation parameters with respective values that can be set by the user via the GUI 64. In some examples, the sub-perception SCS can include a Fast-Acting Sub-Perception Therapy (FAST) program. The FAST program utilizes a stimulation frequency at a level below 100 Hz (or in some instances lower than 10 Hz) and a biphasic-symmetric pulse waveform comprising an active charge phase followed by an active recharge phase. Stimulation pulses in FAST can be defined by stimulation parameters such as stimulation amplitudes, pulse width, frequency, etc. In some examples, sub-perception SCS such as FAST can be delivered in discreet chunks, or boluses of stimulation pulses. Each bolus comprises stimulation pulses delivered during a first duration, followed by a second stimulation-free duration before a next bolus of stimulation pulses are delivered. Such therapy delivered in boluses is generally referred to as a bolus stimulation therapy (BST) in this document. A user may use the GUI 64 to program stimulation settings, such as electrode selection and configuration, stimulation parameter values including, for example, amplitudes, pulse width, frequency, pulse waveform, active or passive recharge mode for FAST, ON time (the first duration), OFF time (the second duration), and therapy duration for BST, among others. In some examples, the user may use the GUI 64 to define criteria for, and initiate a process of, identifying the patient's usage pattern of stimulation, such as frequency, activation time, duration, and manner of using certain stimulation programs (e.g., BST). The identified past stimulation usage pattern can be used to automatically determine or adjust a future stimulation schedule for the patient (or to present to a user a recommendation of such a stimulation schedule), examples of which are discussed below with reference to FIG. 7.

Figure 5:
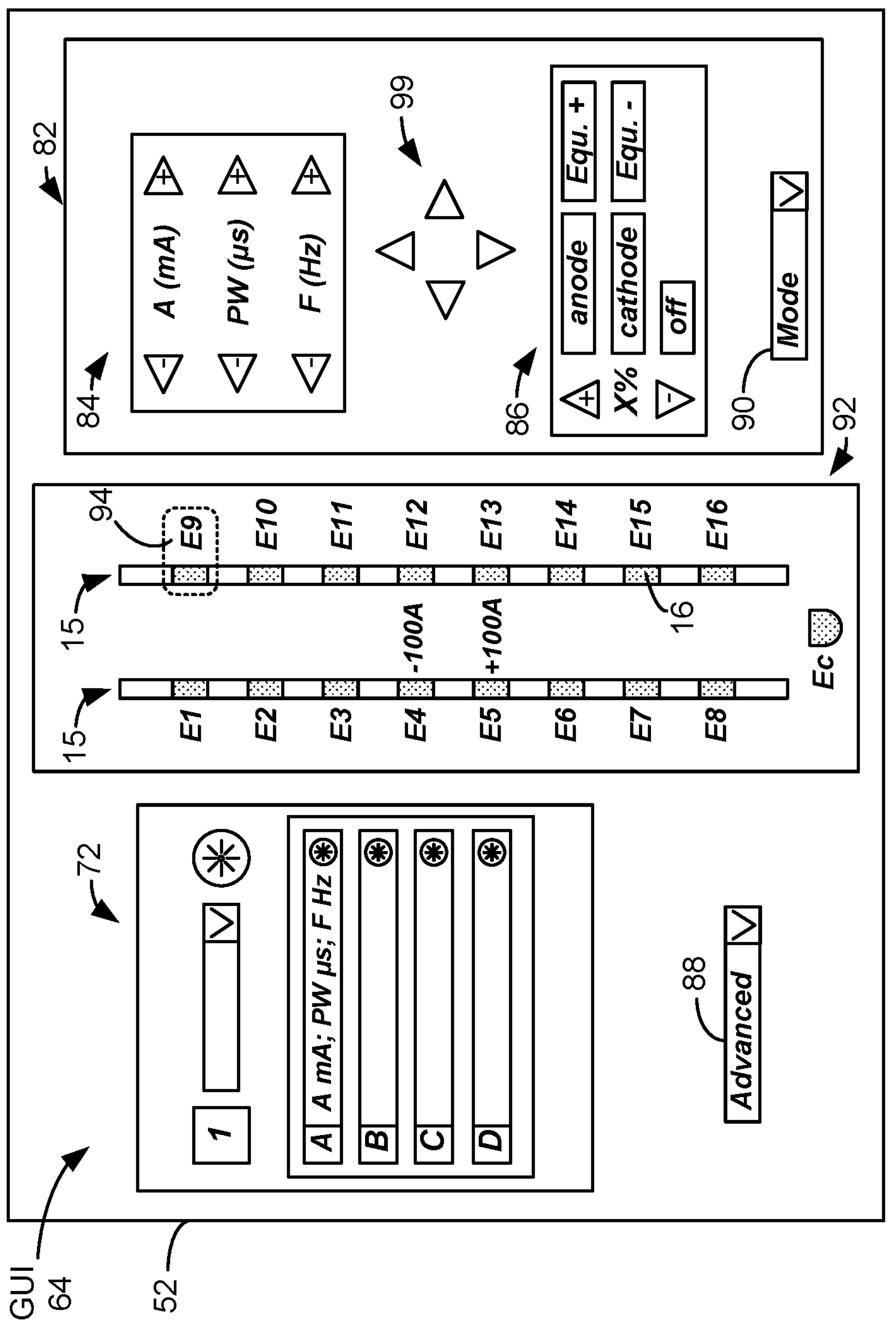
FIG. 5 illustrates, by way of example and not limitation, a Graphical User Interface (GUI) for setting or adjusting stimulation parameters.

FIG. 5 illustrates, by way of example and not limitation, a portion of a GUI (such as one in a clinician programmer) for setting or adjusting stimulation parameters, such as the GUI 64 as shown in FIG. 4. One skilled in the art will understand that the particulars of the GUI 64 will depend on where clinician programmer software 66 is in its execution, which will depend on the GUI selections the clinician has made. FIG. 5 shows the GUI 64 at a point allowing for the setting of stimulation parameters for the patient and for their storage as a stimulation program. To the left a program interface 72 is shown, which as explained further in the '038 Publication allows for naming, loading and saving of stimulation programs for the patient. Shown to the right is a stimulation parameters interface 82, in which specific stimulation parameters (A, D, F, E, P) can be defined for a stimulation program. Values for stimulation parameters relating to the shape of the waveform (A; in this example, current), pulse width (PW), and frequency (F) are shown in a waveform parameter interface 84, including buttons the clinician can use to increase or decrease these values.

Stimulation parameters relating to the electrodes 16 (the electrodes E activated and their polarities P), are made adjustable in an electrode parameter interface 86. Electrode stimulation parameters are also visible and can be manipulated in a leads interface 92 that displays the leads 15 (or 15') in generally their proper position with respect to each other, for example, on the left and right sides of the spinal column. A cursor 94 (or other selection means such as a mouse pointer) can be used to select a particular electrode in the leads interface 92. Buttons in the electrode parameter interface 86 allow the selected electrode (including the case electrode, Ec) to be designated as an anode, a cathode, or off. The electrode parameter interface 86 further allows the relative strength of anodic or cathodic current of the selected electrode to be specified in terms of a percentage, X. This is particularly useful if more than one electrode is to act as an anode or cathode at a given time, as explained in the '038 Publication. In accordance with the example waveforms shown in FIG. 2, as shown in the leads interface 92, electrode E5 has been selected as the only anode to source current, and this electrode receives X=100% of the specified anodic current, +A. Likewise, electrode E4 has been selected as the only cathode to sink current, and this electrode receives X=100% of that cathodic current, −A.

The GUI 64 as shown specifies only a pulse width PW of the first pulse phase 30*a*. The clinician programmer software 66 that runs and receives input from the GUI 64 will nonetheless ensure that the IPG 10 and ETS 40 are programmed to render the stimulation program as biphasic pulses if biphasic pulses are to be used. For example, the clinician programming software 66 can automatically determine durations and amplitudes for both of the pulse phases 30*a* and 30*b* (e.g., each having a duration of PW, and with opposite polarities +A and −A). An advanced menu 88 can also be used (among other things) to define the relative durations and amplitudes of the pulse phases 30*a* and 30*b*, and to allow for other more advance modifications, such as setting of a duty cycle (on/off time) for the stimulation pulses, and a ramp-up time over which stimulation reaches its programmed amplitude (A), etc. A mode menu 90 allows the clinician to choose different modes for determining stimulation parameters. For example, as described in the '038 Publication, mode menu 90 can be used to enable electronic trolling, which comprises an automated programming mode that performs current steering along the electrode array by moving the cathode in a bipolar fashion. While GUI 64 is shown as operating in the CP 50, the user interface of the RC 45 may provide similar functionality.

Figure 6B:
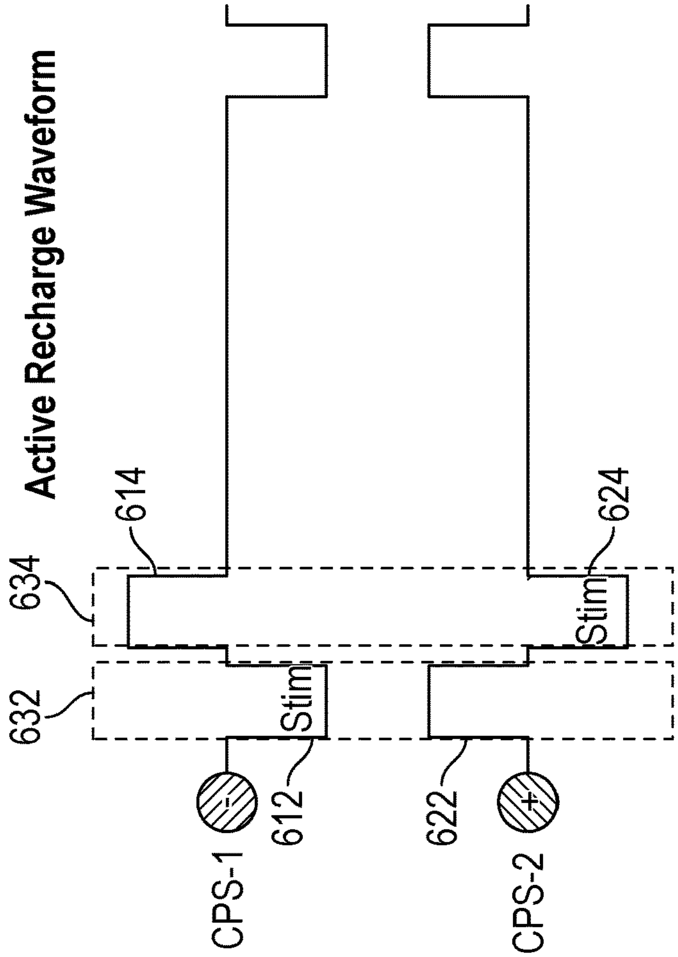
FIGS. 6A-6B illustrate, by way of example and not limitation, schematics of electrode configurations and stimulation waveforms that may be used in Fast-Acting Sub-Perception Therapy (FAST).
Figure 6A:
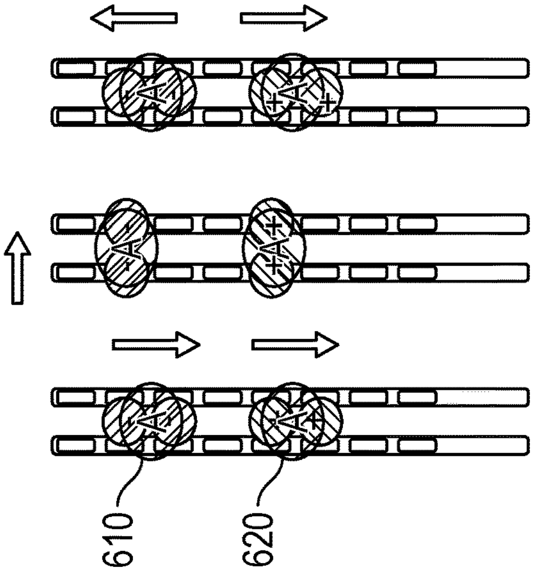

FIGS. 6A-6B illustrate, by way of example and not limitation, schematics of electrode configurations and stimulation waveforms that may be used in Fast-Acting Sub-Perception Therapy (FAST). The FAST can be programmed using a model-based steering algorithm that enables multiple central points of stimulation (CPS) to be moved rostrocaudally and mediolaterally simultaneously at a programmable step set by a user, as illustrated in FIG. 6A. In the illustrated example, by using symmetric biphasic waveforms, two separate CPSs can be implemented in the stimulation paradigm, including CPS-1 610 representing a virtual cathode, and CPS-2 620 representing a virtual anode. CPS-1 610 and CPS-2 620 can respectively sink or source various percentages of total current across multiple electrodes on the lead (also referred to as "current fractionalization"). For example, current applied to the virtual cathode CPS-1 610 can be fractionalized over a plurality of physical cathodes. Similarly, current applied to the virtual anode CPS-2 620 can be fractionalized over a plurality of physician anodes. The bipolar distance between the CPS-1 610 and CPS-2 620 can be programmed to be within a specified range, such as mm. In an example, the bipolar distance is set to approximately 12 mm. The bipolar distance controls the spread of paresthesia during neural target search.

FIG. 6B illustrates biphasic symmetric waveforms of stimulation current for the virtual cathode CPS-1 610 and the virtual anode CPS-2 620. The biphasic symmetric waveform comprises a first charge phase 632, followed by a second active recharge (or charge recovery) phase 634. Current amplitude in each phase remains constant, thus a rectangular waveform. For each of the virtual cathode or the virtual anode, current amplitude of the charge phase 632 has the same magnitude but different sign (representing direction of current flow) than the current amplitude of the recharge phase 634. During the first rectangular phase 632, a negative current 612 (i.e., cathodic current) is injected through negatively configured contacts (physical cathodes corresponding to the virtual cathode CPS-1 610), and positive current 622 (i.e., anodic current) is injected through positively configured return contacts (physical anodes corresponding to the virtual anode CPS-2 620). During the second rectangular phase 634, the polarities of the virtual cathode CPS-1 and the virtual anode CPS-2 are reversed to achieve active charge balance: positive current 614 (i.e., anodic current) is applied to the assigned physical cathodes corresponding to virtual cathode CPS-1 610, and negative current 624 (i.e., cathodic current) is applied to the assigned physical anodes corresponding to virtual anode CPS-2 620.

Stimulation dosing parameters, such as amplitude, frequency (or stimulation rate), pulse width (PW), or waveform pattern of the stimulation waveform are programmable and can be set or adjusted by a user on a GUI. In an example, the frequency of the stimulation pulse (reciprocal of period) can be programmed to a value within a specific range, such as approximately 2-700 Hz. In an example, the stimulation frequency can be programmed to 90 Hz. The pulse width (PW) can be programmed within a range, such as approximately 210±50 micro-seconds (μs). To identify the electrode configuration and fine-tune the location of stimulation, a neural target search can be carried out using the CPS-1 and CPS-2 steered simultaneously in the rostro-caudal and medial-lateral dimensions at a programmable step (resolution) such as in approximately 300 μs increments. The stimulation amplitude can then be lowered to a programmable fraction of the perception threshold. Such a programming for FAST allows for a systematic optimization of the stimulating field that provides comprehensive overlap between the area of pain and paresthesia sensation.

Figure 7:
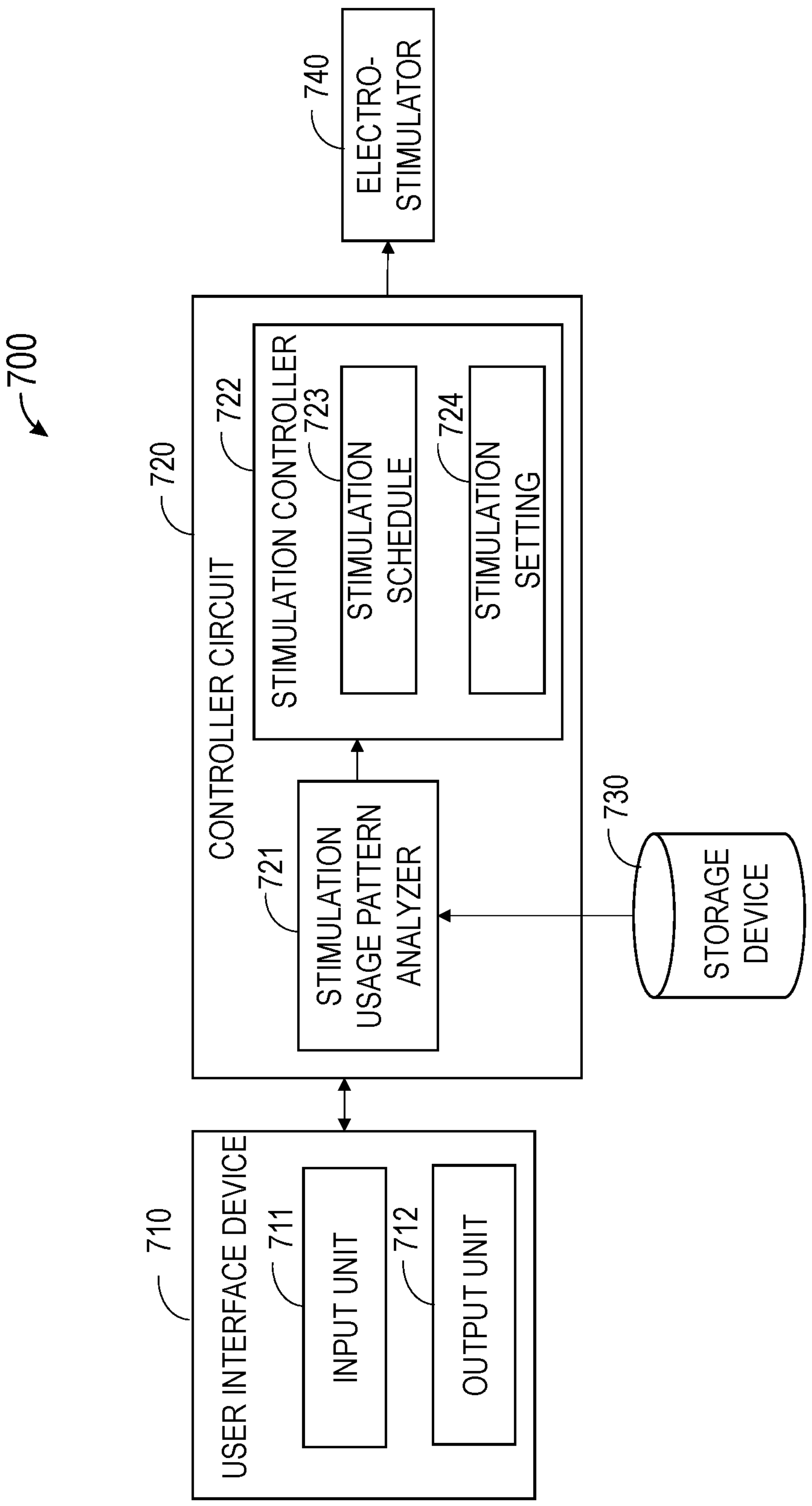
FIG. 7 illustrates, by way of example and not limitation, a neuromodulation system configured to provide or adjust neurostimulation to a neural target based on patient past usage of stimulation programs.

FIG. 7 is a block diagram illustrating, by way of example and not limitation, a neuromodulation system 700 configured to provide or adjust neurostimulation to a neural target based on patient past usage of stimulation programs. In an example, the system 700 can provide spinal cord stimulation (SCS) at a spinal neural target. The SCS can be a part of pain management regimen. In some examples, the system 700 can titrate neurostimulation to treat or alleviate certain autonomic disorders.

The neuromodulation system 700, which is an embodiment of the neuromodulation system 400, may include one or more of a user interface device 710, a controller circuit 720, a storage device 730, and an electrostimulator 740. Portions of the neuromodulation system 700 may be implemented in stimulation devices such as IPG 10 or the ETS 40, and/or controller devices such as the RC 45 or CP 50.

The user interface device 710 can allow a user (e.g., the patient, the physician managing the patient, or a device expert) to program or modify a stimulation setting, and to provide feedback on a stimulation therapy. The feedback can include, for example, therapeutic effectiveness (e.g., pain relief) of a SCS program (e.g., FAST program), and symptoms or side effects experienced by the patient during the therapy. In an example, the user interface device 710 can be a portable (e.g., handheld) device, such as the RC 45 or a smartphone (with executable software application) operable by the patient at his or her home without requiring extra clinic visits or consultation with a device expert. In another example, the user interface device 710 can be a programmer device, such as the CP 50, that allows a physician to remotely review stimulation settings and treatment history, consult with the patient to obtain information including pain relief and SCS-related side effects or symptoms, perform remote programming of the electrostimulator 740, or provide other treatment options to the patient.

The user interface device 710 can include an input unit 711 and an output unit 712. The input unit 711 may include one or more user interface (UI) control elements operable by the user to program or modify a stimulation setting, such as by providing or adjusting values of one or more stimulation parameters, or selecting from a plurality of pre-defined stimulation programs for future use. Each stimulation program can include a set of stimulation parameters with respective pre-determined values. In some examples, the neuromodulation system 700 may automatically determine an "optimal" or improved stimulation setting, or recommend adjustment of one or more stimulation parameters, based on patient past experience, such as a usage pattern of sub-perception SCS stimulation. The usage pattern can be derived from records of past use of stimulation programs provided by the user via the input unit 711. Additionally or alternatively, the records of past use of stimulation programs can be stored in the storage device 730. The storage device 730 can keep a log of patient activation of stimulation programs, such as button presses or other selection means via the UI control elements on the user interface. In some examples, the user may define criteria for identifying the patient's usage pattern via the user interface device 710. Such criteria may include user-specified usage pattern analysis frequency, timing and duration of the stimulation programs used in the past, criteria for identifying similar records in the past, etc., Examples of defining criteria for identifying patient's usage pattern is discussed below with reference to FIG. 8. In some examples, the stimulation setting (including, for example, date, time, duration, stimulation parameter values, or stimulation program for future BST) can be recommended to a user, such as displayed on the output unit 712 of the user interface device 710. The user may accept, reject, or modify the recommended stimulation setting using the input unit 711.

The input unit 711 may include UI control elements operable by the user to provide feedback on the stimulation therapy (e.g., BST). In this document, a stimulation setting can be defined by a set of stimulation parameters with respective programmable or preset values. Examples of the stimulation parameters can include an electrode configuration (e.g., stimulation lead and electrode location, selection of active electrodes, designation of anode and cathode, and stimulation current or energy fractionalization across the electrodes), stimulation dose parameters (e.g., pulse width, frequency, pulse amplitude), stimulation pulse waveform, or an ON-OFF cycling of stimulation bursts, among others. The feedback provided by the user via the input unit 711 can include pain data or feedback on pain relief by the existing SCS therapy. The pain data or the feedback on pain relief may include identification of pain sites, distribution of the pain, intensity of pain at various pain sites, or temporal pattern such as persistence of the pain at various pain sites, a pain drawing with pain markings identifying the locations, intensities, patterns of pain, among other information. In some examples, the feedback may include side effects or symptoms arise or persist associated with the SCS, or severity of the symptom or a side effect. The severity can take a numerical value (e.g., on a 1 to 5 scale) or a categorical value (e.g., "Mild", "Moderate", or "Severe"). The feedback may be provided in different formats, such as texts, graphs, or verbal descriptions, among others. In some examples, the user may provide, via the input unit 711, information about patient health or medical information, such as change in medication, physical activities, medical procedures received, among other information. The stimulation controller 722 may use the user feedback, along with other information, to adjust the stimulation schedule 723, or the stimulation setting 724 (e.g., by changing values for one or more stimulation parameters). Examples of a user interface for the user to provide therapy feedback are discussed below with reference to FIG. 12.

In some examples, in addition or alternative to the feedback provided by the patient, an ambulatory sensor can sense signals indicative of patient responses to the stimulation therapy. The stimulation controller 722 may use the sensor indicated patient responses to adjust the stimulation schedule 723 or the stimulation setting 724 schedule. The ambulatory sensor can be included in, or external to, the IPG 10 or the ETS 40. The ambulatory sensor can sense, for example, cardiac, pulmonary, neural, biochemical, or other physiological signals. Some of these signals may reveal characteristic signal properties in response to an onset, intensity, severity, duration, or patterns of pain. Examples of sensor signals can include cardiac signals such as a heart rate signal, a pulse rate signal, a heart rate variability signal, electrocardiograph (ECG) or intracardiac electrogram, cardiovascular pressure signal, or heart sounds signal, among others. The second signal may additionally or alternatively include a galvanic skin response (GSR) signal, an electrodermal activity (EDA) signal, a skin temperature signal, an electromyogram (EMG) signal, an electroencephalogram (EEG) signal, a magnetoencephelogram (MEG) signal, a hemodynamic signal such as a blood flow signal, a blood pressure signal, a blood perfusion signal, a photoplethysmography (PPG) signal, or a saliva production signal indicating the change of amount of saliva production, among others.

The output unit 712 can include a display to present textually or graphically the information provided by the user via the input unit 711. In an example, the output unit 712 may present to the user an "optimal" or improved stimulation setting or the recommended parameter adjustment. In an example, a future stimulation schedule can be determined based on the patient's usage pattern of stimulation, and presented to the user on the user interface device 710. The user can accept, reject, or modify the stimulation setting or the stimulation schedule via the input unit 711. In some examples, the output unit 712 may display a progress of an ongoing stimulation therapy (e.g., BST) in real time, examples of which are discussed below with reference to FIGS. 11A-11B.

The controller circuit 720, which is an example of the control circuitry 48 of the RC 45 or the control circuitry 70 of the CP 50, can be communicatively coupled to or integrated into the user interface device 710. The controller circuit 720 can determine an "optimal" or improved stimulation setting (as defined by a set of stimulation parameters with respectively optimized values). A stimulation setting is "optima" or improved in the sense that neurostimulation delivered in accordance therewith is likely to achieve a desired therapeutic outcome: avoiding or alleviating the side effects or symptoms associated with present stimulation, while maintaining or improving the pain relief effect. The controller circuit 720 can include circuit sets comprising one or more other circuits or sub-circuits, such as a stimulation usage pattern analyzer 721 and a stimulation controller 722. The circuits or sub-circuits may, alone or in combination, perform the functions, methods, or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

In various examples, portions of the functions of the controller circuit 720 may be implemented as a part of a microprocessor circuit. The microprocessor circuit can be a dedicated processor such as a digital signal processor, application specific integrated circuit (ASIC), microprocessor, or other type of processor for processing information including physical activity information. Alternatively, the microprocessor circuit can be a general purpose processor that can receive and execute a set of instructions of performing the methods or techniques described herein.

Figure 8:
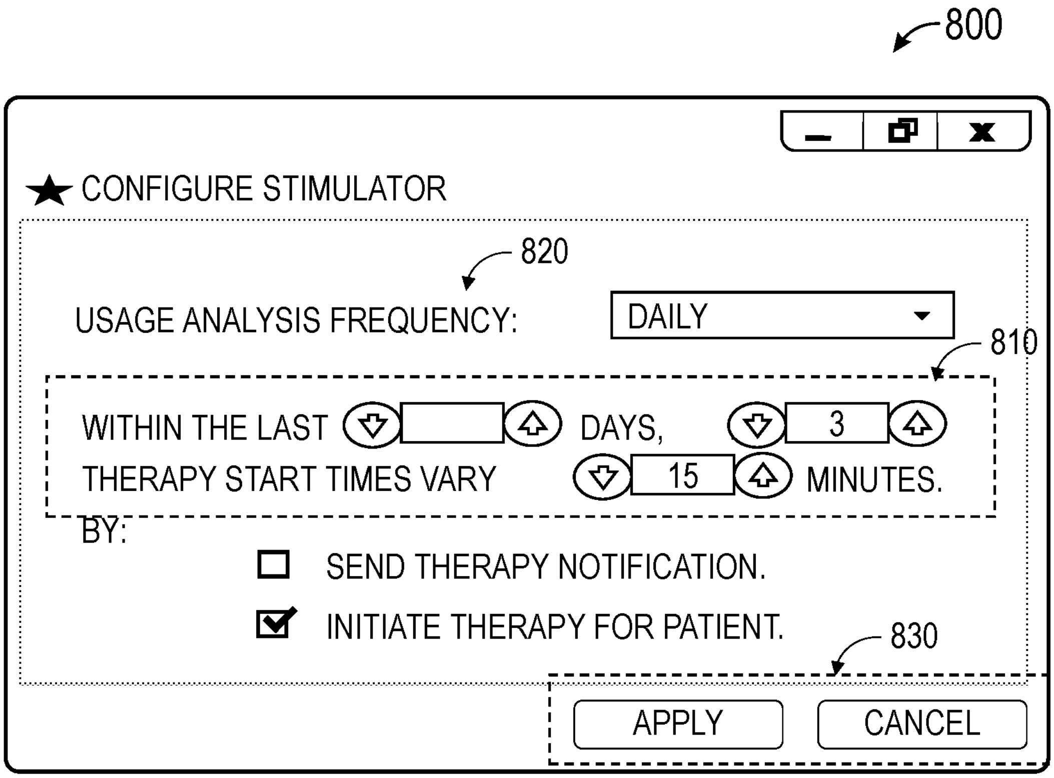
FIG. 8 illustrates a portion of a user interface that receives information about patient past use of the stimulation program and criteria for identifying a usage pattern.

The stimulation usage pattern analyzer 721 may analyze a stimulation usage pattern of the patient based on the information about the patient's past usage of a particular stimulation program, such as a pre-determined stimulation program. Such information about the patient's past usage can be provided by the user via the user interface device 710, or be retrieved from a storage device 730 that stores records of past stimulation usage. In an example, the information about the patient's past usage includes timing or duration for activating a particular stimulation program, such as a BST, during a specific past time period, which can be specified by the user via the user interface device 710. Referring to FIG. 8, a portion of the user interface displays a past stimulation usage analysis window 800 that prompts the user to provide information about the patient past use of a stimulation program, including search criteria 810 for analyzing the patient's stimulation usage pattern. The search criteria 810 can define the time period for analyzing the patient past usage of a stimulation program, and a rule for identifying a majority of substantially consistent timing (e.g., the time of a day) for initiating the stimulation program during a time period in the past. In the illustrated example, the search criteria 810 is defined as, in at least three out of past five days, the stimulation therapy was activated at approximately the same time of the day within a user-defined margin of 15 minutes. The parameters of the search criteria 810, including the time period (e.g., 5 days), the majority threshold (e.g., 3 days), and the margin for the therapy starting time (e.g., 15 minutes) can be specified by the user, or selected from pre-populated values in respective drop-down lists or other UI control elements, as illustrated in FIG. 8. The patient's usage pattern can be analyzed periodically or in an on-demand fashion. For example, the user can specify a usage analysis frequency 820 indicating how often the usage pattern analysis is performed, such as daily (as shown in FIG. 8), every other days, weekly, biweekly, monthly, or other frequencies.

Responsive to a user confirmation 830 to "apply" the search criteria 810, the stimulation usage pattern analyzer 721 can retrieve from the storage device 730 (or prompt the user to input) the patient's past stimulation usage records during the specific time period (e.g., five days). The past usage records can include, for example, the stimulation program used, stimulation parameter values, timing of the stimulation (e.g., time of a day to start the therapy and/or to end the therapy), or therapy duration, among other parameters. The stimulation usage pattern analyzer 721 can search for records that satisfy the search criteria 810, such as those records with substantially the same therapy starting time (within a specified margin of, e.g., ±15 minutes) during the specified time period (e.g., past five days). When records are found to match the search criteria 810 (the "matching records"), the stimulation controller 722 can generate a stimulation schedule 723 that includes a stimulation start time substantially the same as the stimulation start time identified from the matching records. For example, if in the past X out of Y days (e.g., three out of five days), the patient initiates the stimulation therapy at approximately 9:30 a.m. (±15 minutes), then the stimulation controller 722 can determine a future scheduled stimulation start time of approximately 9:30 a.m., or an average, a median, or another central tendency of respective stimulation start times for the "matching records".

Although the stimulation start time of a day is used for identifying the "matching records", this is to be understood as an example but not limitation. Other stimulation parameters (e.g., stimulation duration or other temporal information, stimulation intensity, patient feedback to therapy efficacy such as level of pain relief or symptom relief) can be alternatively or additionally be included in the search criteria 810, and used by the stimulation usage pattern analyzer 721 to identify the "matching records". For example, the stimulation usage pattern analyzer 721 can identify a majority of substantially consistent stimulation duration in the specific time period in the past. The stimulation controller 722 can generate a stimulation schedule 723 based on those "matching records" satisfying the duration requirement. For example, if in the past X out of Y days (e.g., three out of five days), the patient set a particular stimulation program to run for approximately 30 minutes (±5 minutes), then the stimulation controller 722 can determine a future scheduled stimulation duration of approximately 30 minutes, or an average, a median, or another central tendency of respective stimulation duration for the "matching records".

The stimulation controller 722 can additionally determine a stimulation setting 724 including, for example, electrode selection and configuration, stimulation parameter values including, for example, amplitudes, pulse width, frequency, pulse waveform, active or passive recharge mode for FAST, ON time, OFF time, and therapy duration for BST, among others. In an example, the stimulation setting 724 can be determined from those "matching records" identified by the stimulation usage pattern analyzer 721.

The electrostimulator 740 can deliver stimulation in accordance with the stimulation schedule 723 and the stimulation setting 724. The electrostimulator 740 can be an implantable module, such as incorporated within the IPG 10. Alternatively, the electrostimulator 740 can be an external stimulation device, such as incorporated with the ETS 40. In some example, as illustrated in FIG. 8, the user can choose to either send a notification (e.g., to the RC 45 or a smartphone with the patient) for a therapy reminder, or to automatically initiate or adjust stimulation therapy in accordance with the stimulation schedule 723 and the stimulation setting 724. If an automatic therapy initiation is selected, the electrostimulator 740 can deliver stimulation in accordance with the stimulation schedule 723 and the stimulation setting 724.

Figure 9A:
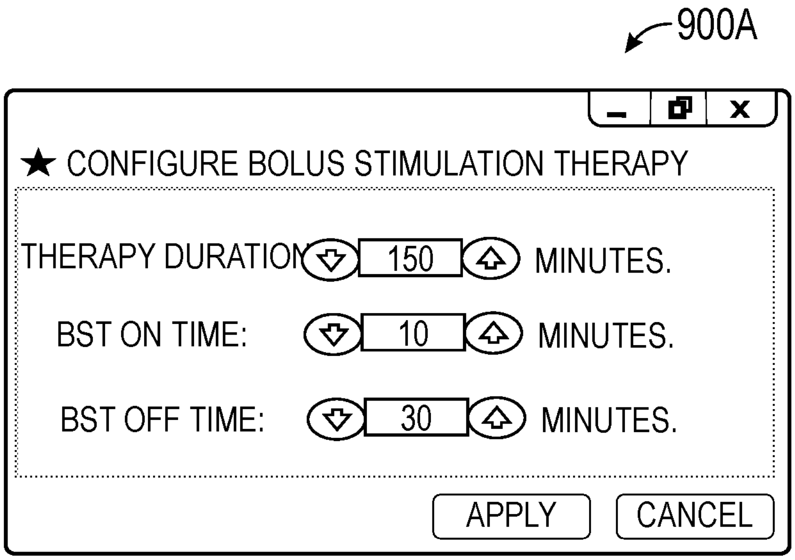
FIGS. 9A-9C illustrate portions of a user interface that receives user programming of stimulation settings or stimulation schedules for a BST.
Figure 9B:
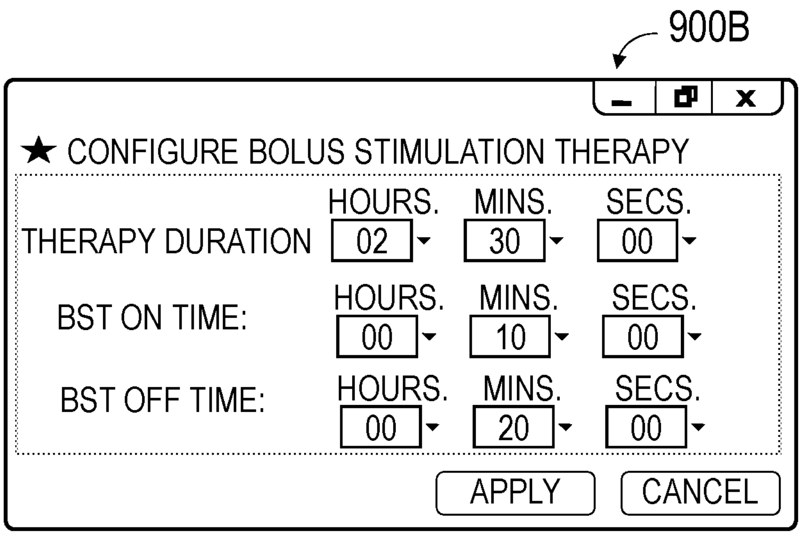
Figure 9C:
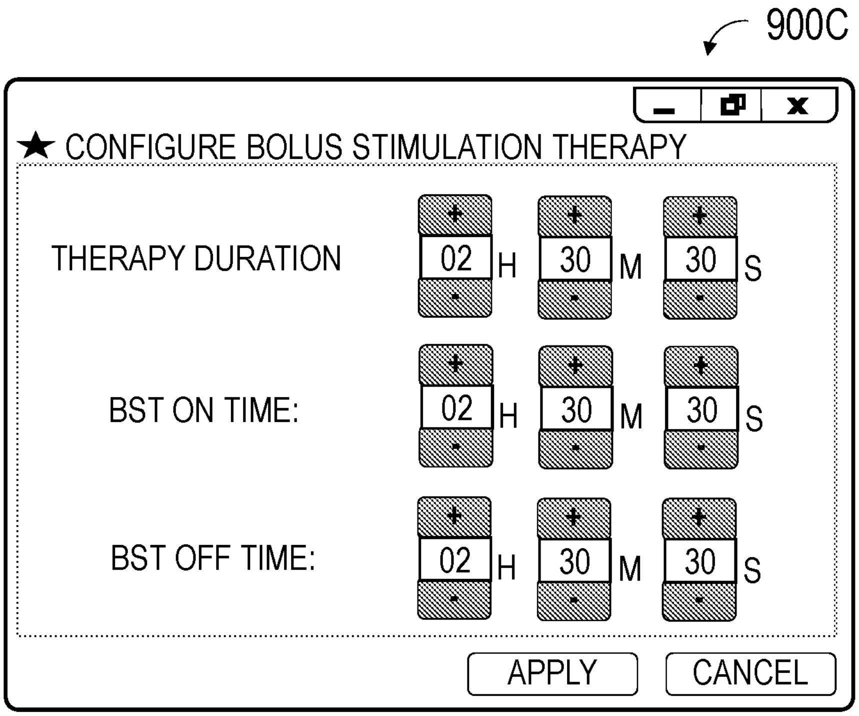

In some examples, the stimulation schedule 723 and/or the stimulation setting 724 can be displayed on the user interface device 710 and recommended to the user. The user can accept, reject, or modify the stimulation schedule 723 and/or the stimulation setting 724. Alternatively, the user can provide a different stimulation schedule or a different stimulation setting than the respective recommendations, via the user interface device 710. Referring to FIGS. 9A-9C, portions of respective user interfaces display stimulation configuration window 900A, 900B, and 900C prompting the user to provide stimulation setting or stimulation schedules, such as stimulation duration, ON time, and OFF times of a bolus stimulation therapy (BST). A bolus of stimulation may be thought of as analogous to a single dose of stimulation, similar to a dose of a pharmaceutical agent. For example, a bolus may comprise stimulation for a first time period (the "ON time"), such as 10 minutes of stimulation (or 30 minutes, or 1 hour, etc.). After a bolus is issued further stimulation is not provided until another bolus is issued. Each bolus comprises a number of periodically-issued pulses at a set frequency. The time period between boluses (the "OFF time") can be on the order of at least minutes, or hours. In some examples, the second period of time may be 30 minutes to 12 hours. In other example, a patient may issue another bolus immediately following a first bolus, just as patient could take a second dose of medication immediately following a first dose.

Some patients respond well to BST. A patient may initiate a bolus of stimulation when they feel pain coming on. Some patients experience extended pain relief, up to several hours or more, following receiving a bolus of stimulation. According to some embodiments, a clinician may prescribe stimulation therapy based on a number of boluses of stimulation. The BST may be programed as a given number of boluses, or as a given therapy duration, per day. As illustrated in FIGS. 9A-9C, a user can input, or select from pre-populated values, one or more of a therapy duration, a BST ON time, and a BST OFF time. In the illustrated example, the BST is scheduled to be delivered for a duration of two hours and 30 minutes, where each bolus has a duration of 10 minutes ("ON time"), with a stimulation-free period of 20 minutes ("OFF time") between any two consecutive boluses. Various UI control elements can be used, including for example, a text box, a drop-down menu, list box, or other selection UI controls, as shown by way of example and not limitation in FIGS. 9A-9C. The electrostimulator 740 can deliver neuromodulation energy in accordance with the user modified or separately provided stimulation setting and/or stimulation schedule.

Figure 13:
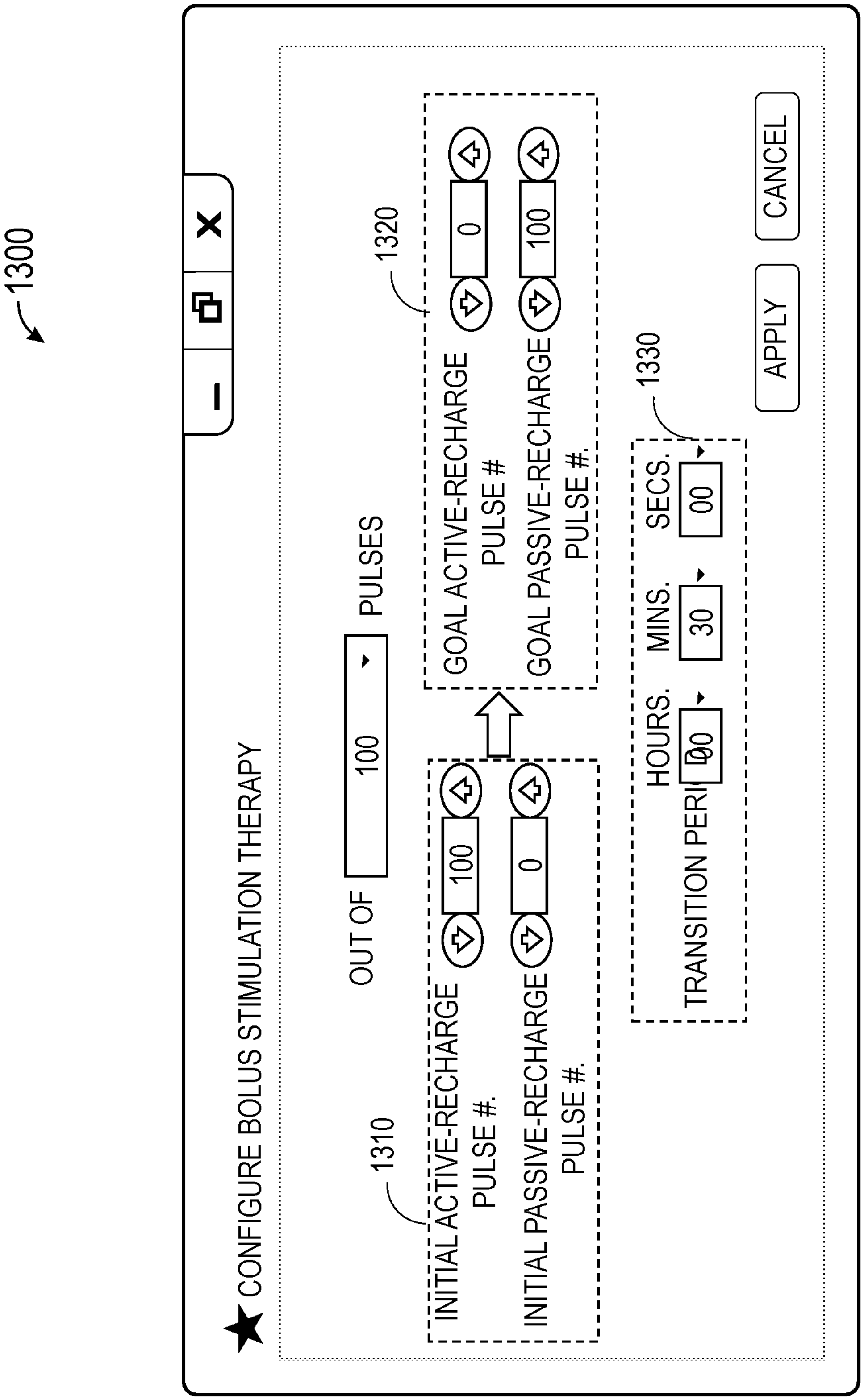
FIG. 13 illustrates a portion of a user interface that displays and prompts the user to program a FAST program with biphasic stimulation pulses having a dynamically reconfigurable recharge phase.

In some examples, the stimulation setting 724 may include a configuration of reconfigurable charge-recharge phases of biphasic stimulation pulses such as used in the FAST program. As stated above, the FAST program utilizes biphasic-symmetric stimulation pulses each comprising an active charge phase followed by an active recharge phase. Compared to conventional sub-perception SCS therapies, FAST can achieve fast-acting analgesia, and significant and long-lasting pain relief. However, the active recharge in FAST program may consume more power than conventional biphasic stimulation pulses with passive recharge phase. To achieve desired therapeutic benefit while keeping the power consumption under control, according to some embodiments, the biphasic stimulation pulses can have a reconfigurable recharge phase that can be set to be either an active recharge phase or a passive recharge phase. If FAST is delivered in boluses, the bolus stimulation can be delivered with a dynamically changing pulse distribution. A pulse distribution be represented by a specified proportion (e.g., X %) of active-recharge pulses or passive-recharge pulses within a bolus or a unit time period, or a specified portion (e.g., number) of active-recharge pulses or a specified portion (e.g., number) of passive-recharge pulses within a specified number of pulses. In an example, BST can be delivered as the pulse distribution dynamically transitions from a first (initial) pulse distribution to a second (goal) pulse distribution different from the first distribution. A user may specify a desired (goal) pulse distribution, or a transition from one pulse distribution (e.g., X % of active-recharge pulse in a bolus, or out of a specified number of N pulses) to another desired pulse distribution (e.g., Y % of active-recharge pulses in a bolus, or out of the N pulses). In some examples, the user may further specific a transition time period, or a rate of transition, from one pulse distribution to another pulse distribution. FIG. 13 illustrates an example of a portion of a user interface 1300 for programming a dynamically changing pulse distribution in a FAST program. The user may program an initial pulse distribution 1310 defined as 100 active-recharge pulses and zero passive-recharge pulses out of 100 pulses (i.e., 100% active-recharge pulses) and a desired (goal) pulse distribution 1320 defined as 100 passive-recharge pulses and zero active-recharge pulses out of 100 pulses (i.e., 100% passive-recharge pulses), and a transition period 1330 (e.g., 30 minutes in this example) for making said transition from all active-recharge pulses to all passive-recharge pulses. In an example, the transition can be linear during the transition period 1330, such that active-recharge pulses are reduced at a rate of approximately three (100/3) pulses per minute, and the passive-recharge pulses are increased at a rate of approximately three (100/3) pulses per minute. Alternatively, in some examples, the transition can be nonlinear, or piecewise linear (i.e., linearly changing pulse distribution at different rates during different time segments). In some example, the user can specify a transition rate (e.g., 5 pulses/minute) as an alternative to the transition period 1330, or a user-specified transition mode (e.g., a nonlinear, or piecewise linear transition). Responsive to a user confirmation to "apply" the dynamically changing pulse distribution as programmed, the stimulation controller 722 can control the electrostimulator 740 to deliver FAST program in accordance with the dynamically changing pulse distribution, such as gradually transitioning from 100% active-recharge pulses to 100% passive-recharge pulses within the specified transition time period (e.g., 30 minutes).

Figure 10:
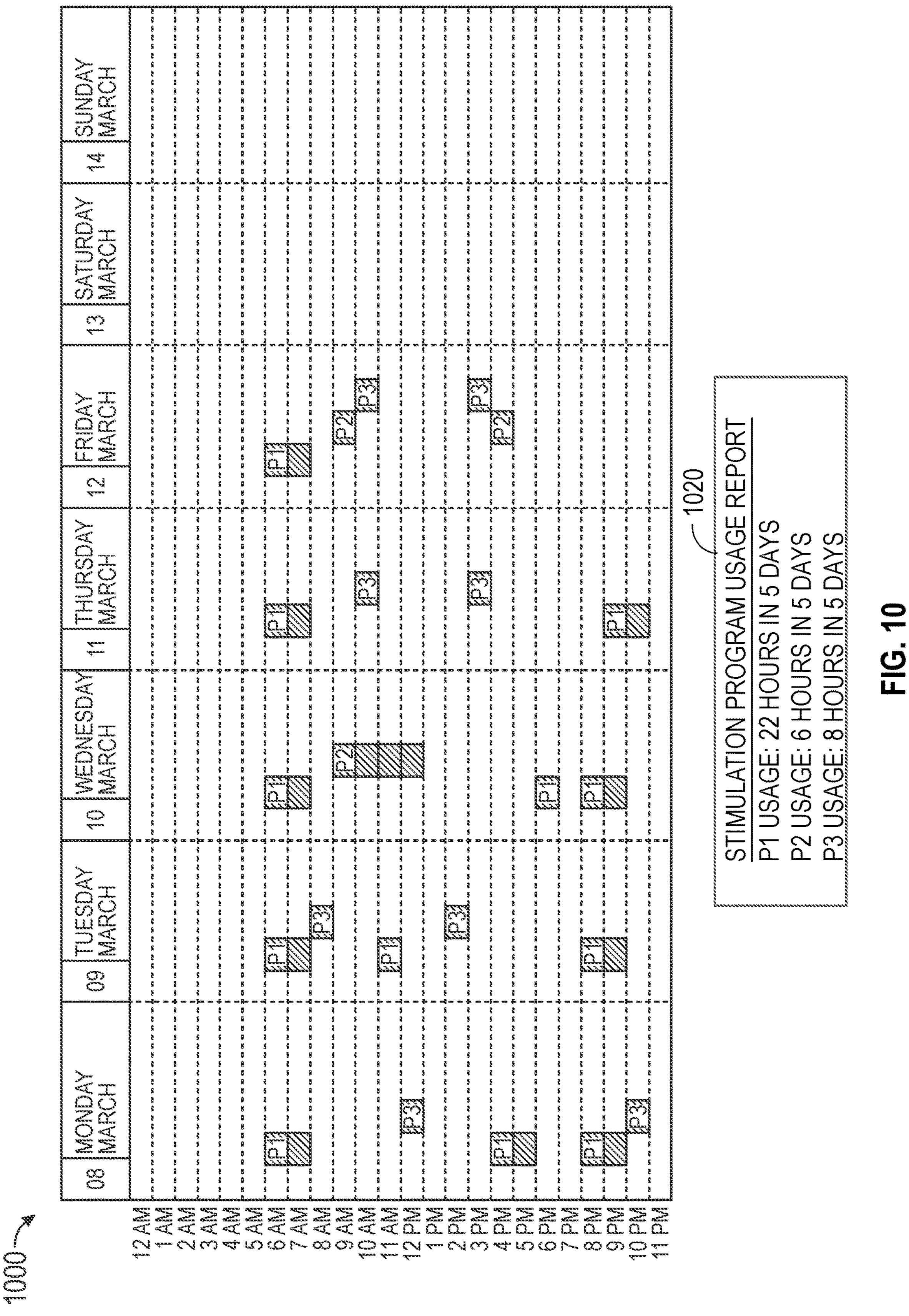
FIG. 10 illustrates a calendar view a stimulation schedule or patient past stimulation usage pattern.

FIG. 10 illustrates portions of a user interface that displays a calendar view 1000 of a stimulation schedule (such as the stimulation schedule 723 generated by the stimulation controller 722) for a patient. Alternatively, the calendar view 1000 can represent the patient's past stimulation usage pattern over a specified time period in the past. In the calendar view 1000, stimulation programs (such as three distinct stimulation programs P1, P2, and P3) scheduled for use in the future can be presented in a format of a daily schedule, a weekly schedule, a biweekly schedule, or a monthly schedule. The distinct stimulation programs P1, P2, and P3 may have different stimulation modes (e.g., sub-perception therapy vs. supra-perception therapy involving paresthesia, bolus therapy vs. continuous therapy, etc.) and/or different stimulation parameter values. The calendar view 1000 may also include timing information such as start time (ON time), end time (OFF time), and/or a duration of each stimulation program. The duration the therapy can be represented by, for example, shaded space in the corresponding time slots in the calendar view 1000. The stimulation programs P1, P2, and P3 may be represented by different patterns, colors, or markers to enhance visual distinctions therebetween. By way of example, FIG. 10 illustrates a weekly schedule in which different respective stimulation programs can be individually and uniquely scheduled for each day of the wee. For example, the Monday schedule includes program P1 from 6:00 a.m.-8:00 a.m., P3 from 11:00 a.m.-12:00 noon; P1 from 4:00 p.m.-5:00 p.m.; P1 from and 8:00 p.m.-10:00 p.m.; and P3 from 10:00 p.m.-11:00 p.m. Scheduling different stimulation programs at different times of a day can be advantageous because a patient's stimulation needs may vary depending on his or her physiological or functional conditions (e.g., physical activities), which may vary on different days over a week. As stated above, the scheduling of the stimulation programs can be based at least on patient usage pattern of one or more stimulation programs, including time of a day to initiate the stimulation program and the stimulation duration.

In some examples, a stimulation program usage report 1020 may be generated and displayed on the user interface. The stimulation program usage report 1020 may include, for example, total time for each of the programs (e.g., P1, P2, and P3) scheduled for the next X days or used in the past X days. In the example shown in FIG. 10, the stimulation program usage report 1020 shows that P1 is scheduled for 22 hours, P2 scheduled for six hours, and P3 scheduled for hours, in five workdays. Other information or statistics about the usage of P1, P2, and P3 can be determined from the calendar view 1000 and shown in the stimulation program usage report 1020.

Figure 11A:
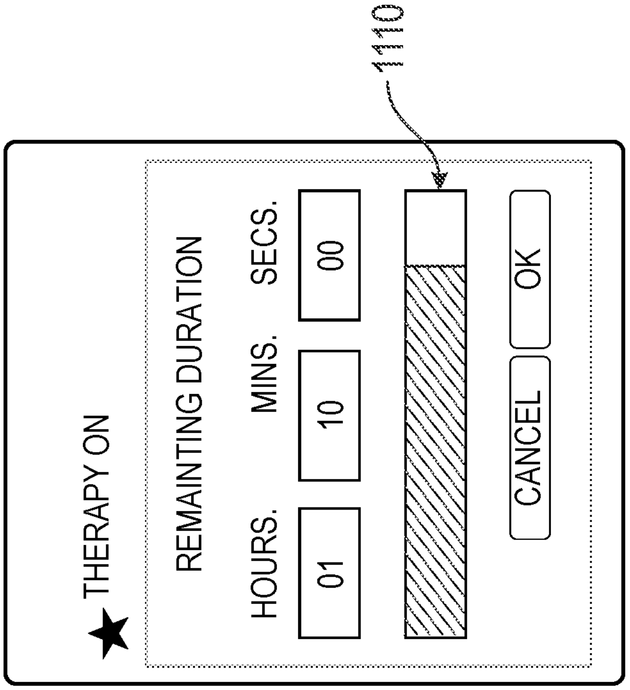
FIGS. 11A-11B illustrate portions of a user interface that displays progress of an ongoing BST being delivered to a neural target of the patient.
Figure 11B:
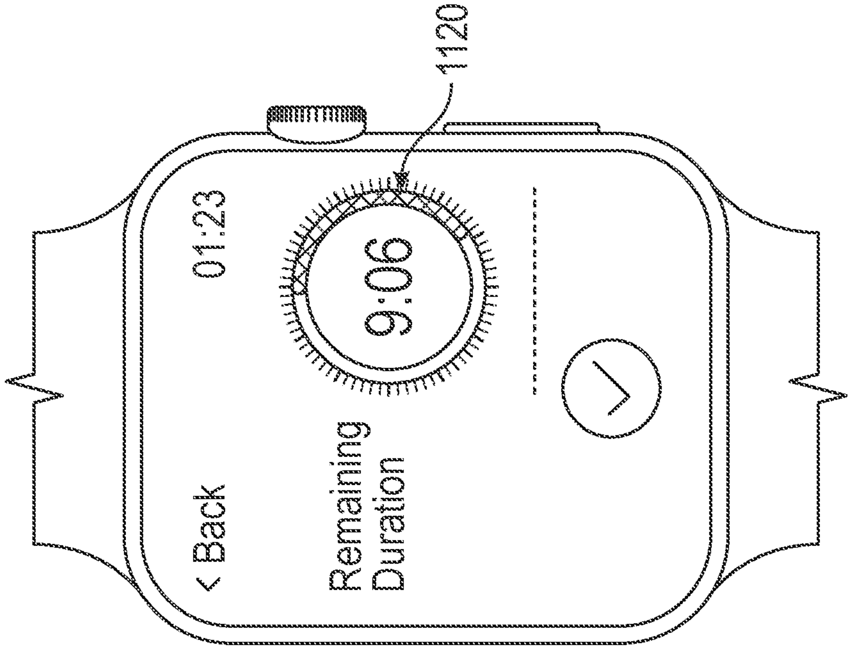

In some examples, the controller circuit 720 can monitor the progress of an ongoing stimulation therapy (e.g., BST) delivered to the patient. The progress can be displayed in real time on the user interface device 710 or otherwise notified to the user, as the stimulation therapy is being delivered to the patient. The stimulation progress can be represented by time remaining for the patient's prescribed therapy. FIG. 11A illustrates a portion of the user interface displaying a linear progress bar 1110 to show time remaining for the current BST therapy. The progress can be represented by other UI elements, or as texts displayed on the user interface. FIG. 11B illustrates a circular progress bar 1120 showing the remaining time of an ongoing BST therapy on a user interface of a smartwatch, which can be an example of the user interface device 710 or the RC 45. In addition or alternative to displaying remaining time, other variables such as an amount of remaining charge or variables related thereto can be displayed. Tracking the progress of a prescribed therapy gives the user (e.g., the patient) more control of optimizing the stimulation therapy. For example, if pain is effectively controlled before the scheduled therapy duration, the user may determine a more suitable therapy duration (shorter than the scheduled one), and make relevant adjustment for future therapies. The user may also cancel the remainder of the prescribed therapy from the user interface.

Figure 12:
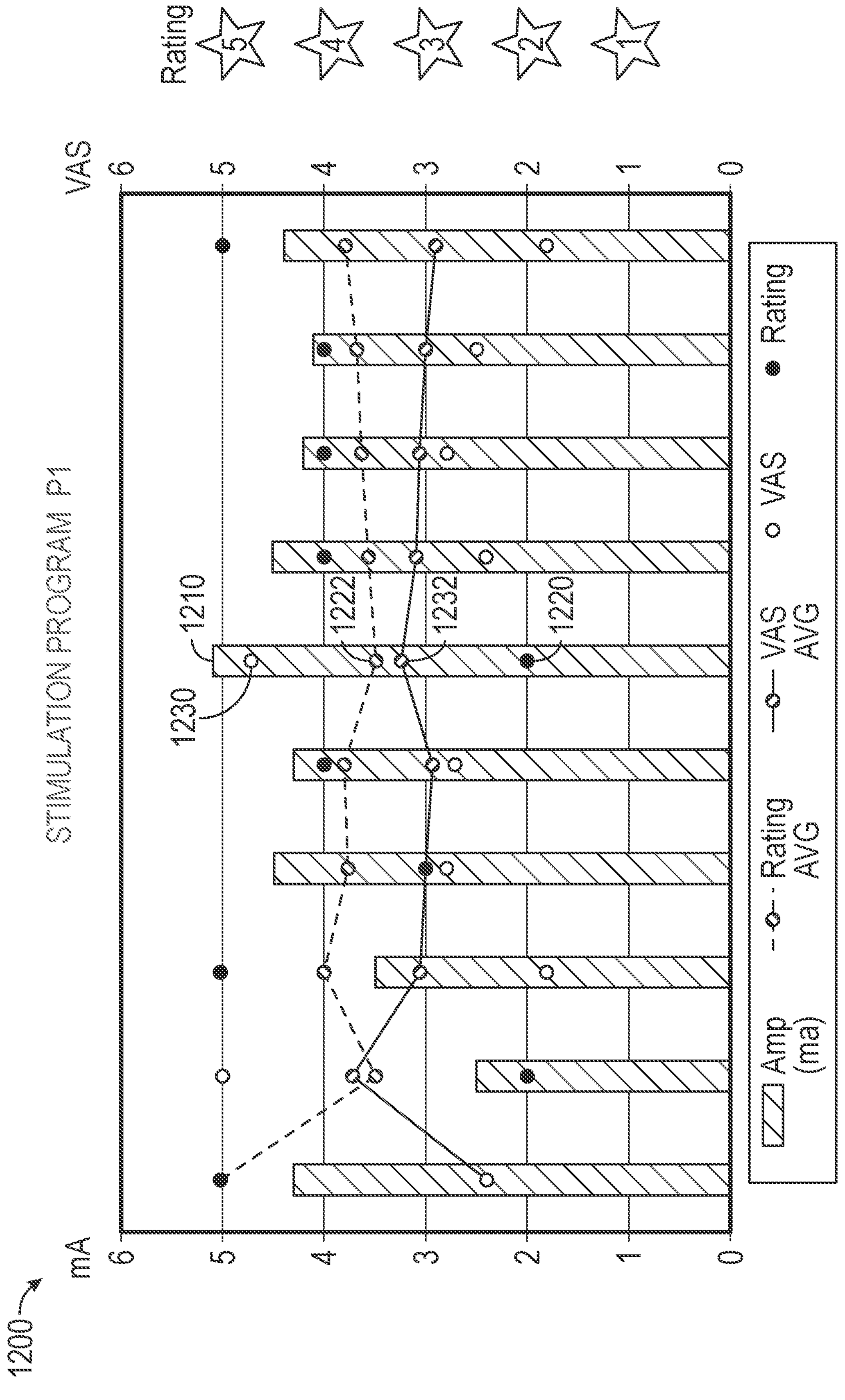
FIG. 12 illustrates, by way of example and not limitation, a graphical representation of user feedback on a stimulation program.

FIG. 12 illustrates an example graphical representation of user feedback 1200 on a stimulation program "P1". The user feedback can be provided by the user (e.g., the patient) via the RC 45 or a smartphone, and displayed on the output unit 712 of the user interface device 710. The user feedback 1200 represents a clinical effect of the stimulation program "P1". As illustrated in FIG. 12, the user feedback 1200 can include information about stimulation settings (e.g., stimulation parameter values) of the stimulation program "P1" and user feedback on the therapy delivered in accordance with the stimulation program "P1" over a specific time period in the past. By way of example and not limitation, the stimulation parameter can include a stimulation current amplitude. Different stimulation amplitude values 1210 may be used in the stimulation program "P1". The user feedback can be provided in the format of rating scores 1220 corresponding to each of the stimulation amplitude values 1210. The rating scores 1220 represents an overall satisfaction of the therapy at a particular stimulation amplitude. The rating score can take discrete values within a specific range, such as between 1 and 5. In some examples, the user feedback may additionally or alternatively include pain scores, such as represented by Visual Analogue Scale (VAS) scores 1230. The VAS is a psychometric response scale that can be used in questionnaires. It is a measurement instrument for subjective characteristics or attitudes that cannot be directly measured. When responding to a VAS item, respondents specify their level of agreement to a statement by indicating a position along a continuous line between two end points. The VAS can be used to measure pain intensity, frequency, progression, or compare pain severity between paints with similar conditions. The VAS score can take continuous ("analogue") values within a specific range, such as between 0 and 5.

As patient's rating of a therapy, or a VAS score for pain, may vary even for pain therapies with the same stimulation intensity, different measurements of rating scores 1220 and/or different measurements of VAS scores 1230 can be obtained from past therapies within the specific time period. At each stimulation current intensity value, an average rating score 1222 can be determined using the rating scores 1220 at that stimulation current amplitude. Similarly, an average VAS score 1232 can be determined using the VAS scores 1230 at that stimulation current intensity. The graphical user feedback 1200, when displayed to the user, provides a visual guide to the user to determine or adjust stimulation current amplitude. For example, the stimulation current amplitude that corresponds to a high average rating score (high therapy satisfaction) and/or a low average VAS score (less pain, or more significant pain reduction) can be selected to be included in a future stimulation program.

Figure 14:
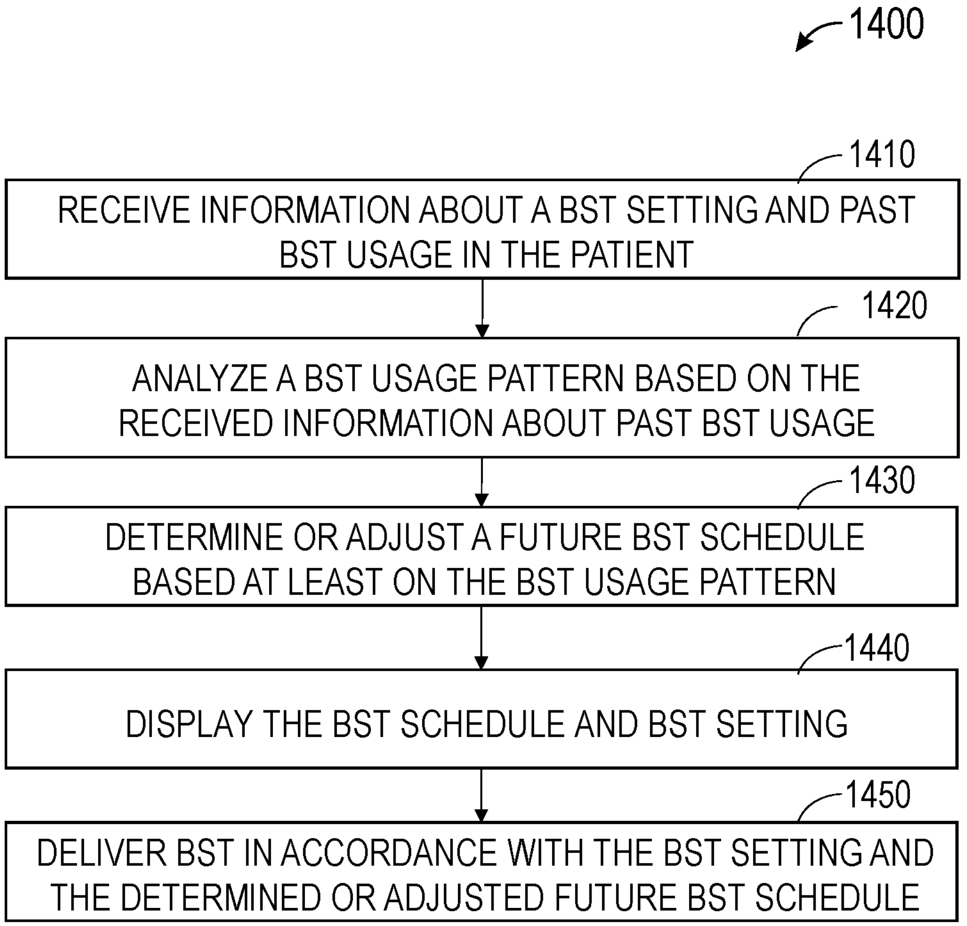
FIG. 14 is a flow chart illustrating, by way of example and not limitation, a method for providing a bolus stimulation therapy (BST) to a patient based on patient past therapy usage pattern.

FIG. 14 is a flow chart illustrating, by way of example and not limitation, a method 1400 a method for providing a bolus stimulation therapy (BST) to a patient based on patient past therapy usage pattern. The method 1400 may be carried out using a medical system such as the neuromodulation system 400 or the neuromodulation system 700. Portions of the method 1400 may be implemented in an external device, such as the RC 45 or the CP 50. In an example, the method 1400 may be used to program and provide spinal cord stimulation (SCS) at a spinal neural target. The SCS can be a part of pain management regimen. By executing the method 1400, the programming device or the external device may program a neuromodulation device (e.g., the IPG 10, the ETS 40, or the electrostimulator 740) to deliver stimulation to various spinal neural targets. Additionally or alternatively, the method 1400 may be used to titrate SCS to treat or alleviate certain autonomic disorders.

At 1410, information about a BST setting and past BST usage in the patient may be received such as from a user input device (e.g., the user interface device 710) or from a storage device (e.g., the storage device 730). The BST setting can be defined by a set of stimulation parameters with respective programmable or preset values. Examples of the stimulation parameters can include an electrode configuration (e.g., stimulation lead and electrode location, selection of active electrodes, designation of anode and cathode, and stimulation current or energy fractionalization across the electrodes), stimulation dose parameters (e.g., pulse width, frequency, pulse amplitude), stimulation pulse waveform, or an ON-OFF cycling of stimulation bursts (comprising a pulse train during an ON period, followed by a pulse-free period during an OFF period), among others. Information about the patient's past BST usage can include BST ON time, BST OFF time, and therapy duration during a specific past time period.

At 1420, a BST usage pattern can be analyzed based on the received information about the past BST usage, such as using the stimulation usage pattern analyzer 721. The analysis of the BST usage pattern can include identifying, from the received past BST usage information, records that satisfy "search criteria" which can be defined by a user via the user interface, such as the search criteria 810 as described above with reference to FIG. 8. The search criteria can define the time period for analyzing the patient past usage of a stimulation program, and a rule for identifying a majority of substantially consistent timing (e.g., the time of a day) for initiating the stimulation program during a time period in the past. In some examples, the search criteria may be defined based on other stimulation parameter (e.g., stimulation duration or other temporal information, stimulation intensity, patient feedback to therapy efficacy such as level of pain relief or symptom relief).

When records are found to match the search criteria (the "matching records"), a future BST schedule can be determined or adjusted at 1430 based at least on the BST usage pattern identified from the matching records. In an example, the future BST schedule can include a stimulation start time substantially the same as the stimulation start time identified from the matching records. For example, if in the past three out of five days, the patient initiates BST therapy at approximately 9:30 a.m. (±15 minutes), then the future BST scheduled can include a BST start time of approximately 9:30 a.m., or an average, a median, or another central tendency of respective stimulation start times for the "matching records".

In some examples, patient feedback on the BST therapy can be received from the user interface. The patient feedback may include pain data or feedback on pain relief, side effects or symptoms, or severity of the symptom or a side effect. The patient feedback can be provided in the format of rating scores represents an overall satisfaction of the BST therapy, or a pain score such as represented by Visual Analogue Scale (VAS) scores, as discussed above with reference to FIG. 12. In some examples, an ambulatory sensor can sense signals indicative of patient responses to the stimulation therapy. The patient feedback and/or sensor-indicated patient responses can be used to adjust the BST setting or the future BST schedule.

In some examples, the BST setting may include a configuration of biphasic stimulation pulses such as used in the FAST program. The biphasic stimulation pulses can have reconfigurable recharge phases that can be set to be either an active recharge phase or a passive recharge phase. When FAST is delivered in boluses in a BST, the bolus stimulation can be delivered with a dynamically changing pulse distribution. For example, the BST can be delivered as the pulse distribution dynamically transitions from a first (initial) pulse distribution to a second (goal) pulse distribution different from the first distribution. A user may specify a desired (goal) pulse distribution, or a transition from one pulse distribution (e.g., X % of active-recharge pulse in a bolus, or out of a specified number of N pulses) to another desired pulse distribution (e.g., Y % of active-recharge pulses in a bolus, or out of the N pulses), as described above with reference to FIG. 13. The dynamically changing pulse distribution can be programmed to the electrostimulator to provide BST in accordance with the dynamically changing pulse distribution, such as gradually transitioning from 100% active-recharge pulses to 100% passive-recharge pulses within the specified transition time period.

At 1440, the BST schedule and the BST setting can be displayed on a user interface. In an example, the BST schedule can be presented in a calendar view that presents stimulation programs scheduled for use in the future. The calendar view can be presented in a format of a daily schedule, a weekly schedule, a biweekly schedule, or a monthly schedule, as illustrated in FIG. 10. In some examples, patient's past stimulation usage pattern can also be displayed on the user interface and presented in a calendar view. In some examples, a progress of an ongoing BST delivered to the patient can be monitored, and the progress can be displayed in real time on the user interface, as illustrated in FIG. 11A-11B.

At 1450, BST can be delivered to the patient via an electrostimulator (e.g., g, the IPG 10, the ETS 40, or the electrostimulator 740) in accordance with the BST setting and the determined or adjusted future BST schedule. In some example, as illustrated in FIG. 8, the user can choose to either send a notification for a therapy reminder, or to automatically initiate or adjust the BST therapy. In some examples, the user interface may prompt the user to provide feedback on the current stimulation setting, such as an indication of a level of satisfaction with respect to pain relief and symptom control. Acknowledgement of user feedback and further recommendations may be generated and display to the user, depending on the user satisfaction level. Existing stimulation setting can remain unchanged for future use if the patient is satisfied with the therapy and symptom relief, and a different setting can be generated and recommend to the user if the patient is not satisfied with the current setting.

Figure 15:
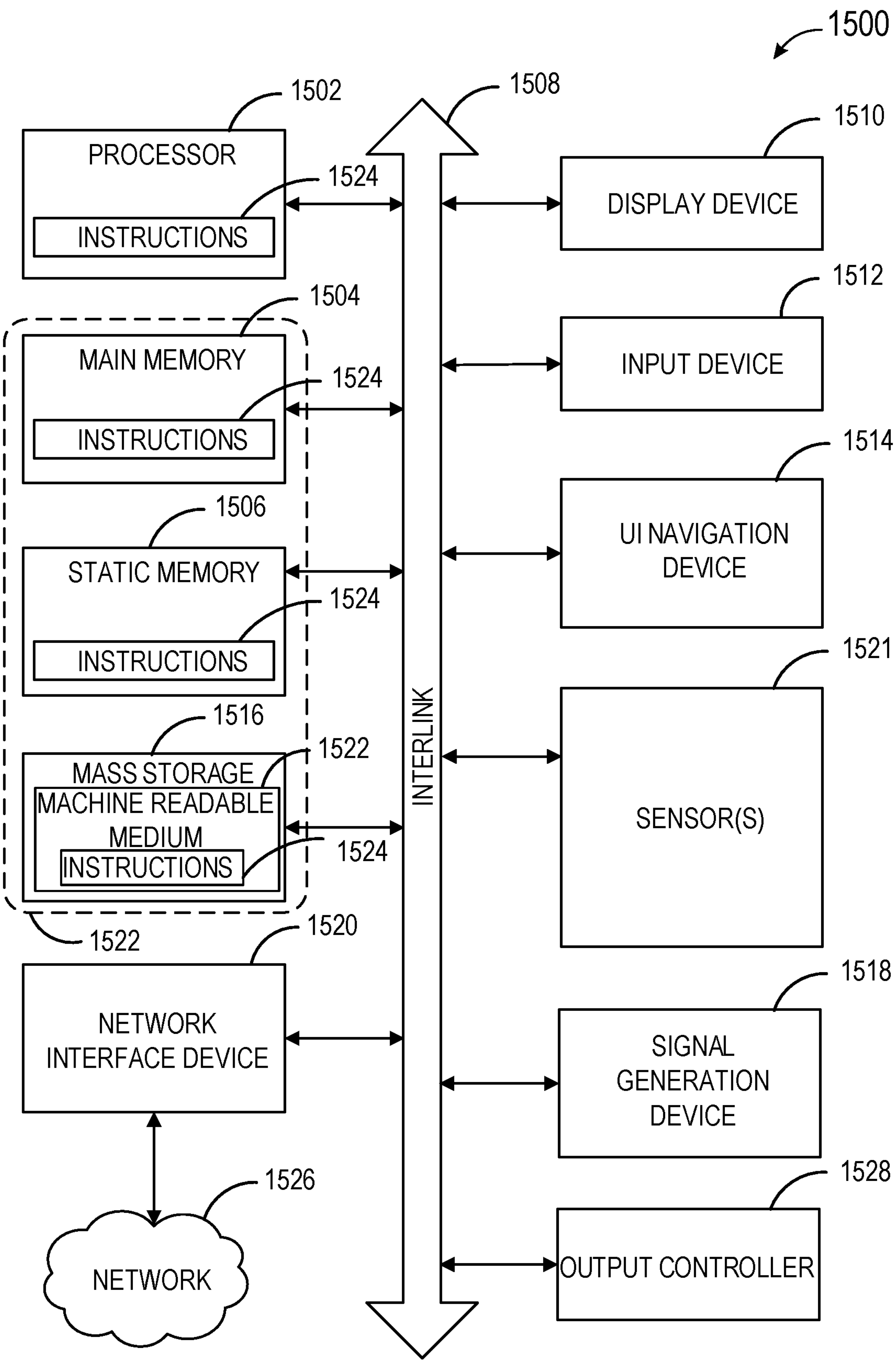
FIG. 15 illustrates generally a block diagram of an example machine upon which any one or more of the techniques (e.g., methodologies) discussed herein may perform.

FIG. 15 illustrates generally a block diagram of an example machine 1500 upon which any one or more of the techniques (e.g., methodologies) discussed herein may perform. Portions of this description may apply to the computing framework of various portions of the neuromodulation device or the external programming device.

In alternative examples, the machine 1500 may operate as a standalone device or may be connected (e.g., networked) to other machines. In a networked deployment, the machine 1500 may operate in the capacity of a server machine, a client machine, or both in server-client network environments. In an example, the machine 1500 may act as a peer machine in peer-to-peer (P2P) (or other distributed) network environment. The machine 1500 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), among other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 1500 may include a hardware processor 1502 (e.g., a central processing unit (CPU), a graphics processing unit (GPU), a hardware processor core, algorithm specific ASIC, or any combination thereof), a main memory 1504 and a static memory 1506, some or all of which may communicate with each other via an interlink (e.g., bus) 1508. The machine 1500 may further include a display unit 1510 (e.g., a raster display, vector display, holographic display, etc.), an alphanumeric input device 1512 (e.g., a keyboard), and a user interface (UI) navigation device 1514 (e.g., a mouse). In an example, the display unit 1510, input device 1512 and UI navigation device 1514 may be a touch screen display. The machine 1500 may additionally include a storage device (e.g., drive unit) 1516, a signal generation device 1518 (e.g., a speaker), a network interface device 1520, and one or more sensors 1521, such as a global positioning system (GPS) sensor, compass, accelerometer, or other sensors. The machine 1500 may include an output controller 1528, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 1516 may include a machine readable medium 1522 on which is stored one or more sets of data structures or instructions 1524 (e.g., software) embodying or utilized by any one or more of the techniques or functions described herein. The instructions 1524 may also reside, completely or at least partially, within the main memory 1504, within static memory 1506, or within the hardware processor 1502 during execution thereof by the machine 1500. In an example, one or any combination of the hardware processor 1502, the main memory 1504, the static memory 1506, or the storage device 1516 may constitute machine readable media.

While the machine-readable medium 1522 is illustrated as a single medium, the term "machine readable medium" may include a single medium or multiple media (e.g., a centralized or distributed database, and/or associated caches and servers) configured to store the one or more instructions 1524.

The term "machine readable medium" may include any medium that is capable of storing, encoding, or carrying instructions for execution by the machine 1500 and that cause the machine 1500 to perform any one or more of the techniques of the present disclosure, or that is capable of storing, encoding or carrying data structures used by or associated with such instructions. Non-limiting machine-readable medium examples may include solid-state memories, and optical and magnetic media. In an example, a massed machine-readable medium comprises a machine readable medium with a plurality of particles having invariant (e.g., rest) mass. Accordingly, massed machine-readable media are not transitory propagating signals. Specific examples of massed machine-readable media may include: non-volatile memory, such as semiconductor memory devices (e.g., Electrically Programmable Read-Only Memory (EPROM), Electrically Erasable Programmable Read-Only Memory (EPSOM)) and flash memory devices; magnetic disks, such as internal hard disks and removable disks; magneto-optical disks; and CD-ROM and DVD-ROM disks.

The instructions 1524 may further be transmitted or received over a communication network 1526 using a transmission medium via the network interface device 1520 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 1520 may include one or more physical jacks (e.g., Ethernet, coaxial, or phone jacks) or one or more antennas to connect to the communication network 1526. In an example, the network interface device 1520 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 1500, and includes digital or analog communications signals or other intangible medium to facilitate communication of such software.

Various examples are illustrated in the figures above. One or more features from one or more of these examples may be combined to form other examples.

The method examples described herein may be machine or computer-implemented at least in part. Some examples may include a computer-readable medium or machine-readable medium encoded with instructions operable to configure an electronic device or system to perform methods as described in the above examples. An implementation of such methods may include code, such as microcode, assembly language code, a higher-level language code, or the like. Such code may include computer readable instructions for performing various methods. The code may form portions of computer program products. Further, the code may be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. A system for providing electrostimulation to a patient, comprising:

an electrostimulator configured to provide a bolus stimulation therapy (BST) to a neural target of the patient, the BST comprising boluses of stimulation each comprising stimulation pulses delivered during a first duration to the neural target, any two consecutive boluses being separated by a stimulation-free second duration; and a controller circuit configured to:

receive information about a BST setting and past BST usage in the patient;

analyze a BST usage pattern based on the received information about the past BST usage;

determine or adjust a future BST schedule based at least on the BST usage pattern; and generate a control signal to the electrostimulator to deliver BST to the neural target in accordance with the BST setting and the determined or adjusted future BST schedule.

2. The system of claim 1, wherein the received information about the past BST usage includes timing or duration for activating the BST during a past time period, wherein the controller circuit is configured to analyze the BST usage pattern to identify a majority of substantially consistent timing or duration for activating the BST during the past time period, and to determine or adjust the future BST schedule including a future timing or duration for activating the BST based on the identified majority of substantially consistent timing or duration.

3. The system of claim 2, wherein the controller circuit is configured to analyze the BST usage pattern at a user-specified frequency.

4. The system of claim 1, wherein the received information about the past BST usage includes information about usage of a specific stimulation program during a past time period, wherein the controller circuit is configured to analyze the BST usage pattern to determine a frequent use of the specific stimulation program.

5. The system of claim 4, wherein the specific stimulation program includes a sub-perception stimulation program comprising biphasic pulses each including an active charge phase and a subsequent reconfigurable active or passive recharge phase.

6. The system of claim 5, wherein the sub-perception stimulation program comprises, within a bolus of a plurality of the biphasic pulses, a first portion of biphasic pulses each having an active recharge phase and a second portion of the biphasic pulses each having a passive recharge phase, wherein the controller circuit is configured to determine or adjust the future BST schedule by decreasing a first number of the biphasic pulses with active recharge phases or increasing a second number of biphasic pulses with passive recharge phases over time.

7. The system of claim 6, wherein the controller circuit is configured to decrease the first number or to increase the second number at respective adjustable rates.

8. The system of claim 1, wherein the controller circuit is configured to determine or adjust the future BST schedule further based on information about patient response to the BST delivered to the neural target.

9. The system of claim 8, comprising an ambulatory sensor configured to sense signals indicative of the patient response to the BST delivered to the neural target, wherein the controller circuit is configured to determine or adjust the future BST schedule further based on the sensed signals.

10. The system of claim 1, wherein the controller circuit is configured to receive the information about the BST setting and the past BST usage from a storage device configured to automatically store information about BST being delivered to the neural target.

11. The system of claim 1, comprising a user interface device communicatively coupled to the controller circuit, the user interface device configured to, under a control of the controller circuit, display a calendar view of one or more of the BST usage pattern or the determined or adjusted future BST schedule.

12. The system of claim 11, wherein the user interface device is configured to:

display the determined or adjusted future BST schedule including a recommendation for date, time, duration, stimulation parameter values, or stimulation program; and receive a user input to confirm, reject, or modify the recommendation.

13. The system of claim 11, wherein the user interface device is configured to display a progress of the BST being delivered to the neural target of the patient.

14. A method for providing a bolus stimulation therapy (BST) to a patient, the method comprising:

receiving, from a user input device or a storage device, information about a BST setting and past BST usage in the patient;

analyzing a BST usage pattern based on the received information about the past BST usage;

determining or adjusting a future BST schedule based at least on the BST usage pattern; and delivering BST to a neural target of the patient in accordance with the BST setting and the determined or adjusted future BST schedule using an electrostimulator, the BST comprising boluses of stimulation each comprising stimulation pulses delivered during a first duration to the neural target, any two consecutive boluses being separated by a stimulation-free second duration.

15. The method of claim 14, wherein the received information about the past BST usage includes timing or duration for activating the BST during a past time period, and wherein analyzing the BST usage pattern includes identifying a majority of substantially consistent timing or duration for activating the BST during the past time period;

wherein determining or adjusting the future BST schedule includes determining or adjusting a future timing or duration for activating the BST based on the identified majority of substantially consistent timing or duration.

16. The method of claim 14, wherein the received information about the past BST usage includes information about usage of a specific stimulation program during a past time period, wherein analyzing the BST usage pattern includes determining a frequent use of the specific stimulation program.

17. The method of claim 16, wherein the specific stimulation program includes a sub-perception stimulation program comprising biphasic pulses each including an active charge phase and a subsequent reconfigurable active or passive recharge phase.

18. The method of claim 17, wherein the sub-perception stimulation program comprises, within a bolus of a plurality of biphasic pulses, a first portion of the biphasic pulses each having an active recharge phase and a second portion of the biphasic pulses each having a passive recharge phase, wherein determining or adjusting the future BST schedule includes decreasing a first number of the biphasic pulses with active recharge phases or increasing a second number of biphasic pulses with passive recharge phases over time.

19. The method of claim 18, wherein decreasing the first number or increasing the second number over time are in accordance with respective adjustable rates.

20. The method of claim 14, comprising displaying, on a user interface device, a calendar view of one or more of the BST usage pattern or the determined or adjusted future BST schedule.

* * * * *